United States Patent
Quinn et al.

(10) Patent No.: US 8,133,242 B1
(45) Date of Patent: Mar. 13, 2012

(54) IMAGE-GUIDED EXTRALUMINAL OCCLUSION

(75) Inventors: Stephen F. Quinn, Eugene, OR (US); Ross S. Tsugita, Mountain View, CA (US)

(73) Assignee: Q-Tech Medical Incorporated, Eugene, OR (US)

( * ) Notice: Subject to any disclaimer, the term of this patent is extended or adjusted under 35 U.S.C. 154(b) by 341 days.

(21) Appl. No.: 11/740,945

(22) Filed: Apr. 27, 2007

(51) Int. Cl.
*A61B 17/08* (2006.01)
*A61B 17/10* (2006.01)

(52) U.S. Cl. ......................................... 606/157; 606/142
(58) Field of Classification Search ................... 606/157, 606/142; 600/462, 463
See application file for complete search history.

(56) References Cited

U.S. PATENT DOCUMENTS

| | | | |
|---|---|---|---|
| 3,840,018 A | 10/1974 | Heifetz | |
| 3,877,434 A | 4/1975 | Ferguson et al. | |
| 3,996,937 A | 12/1976 | Williams | |
| 4,069,825 A | 1/1978 | Akiyama | |
| 4,394,864 A | 7/1983 | Sandhaus | |
| 4,458,682 A | 7/1984 | Cerwin | |
| 4,471,766 A | 9/1984 | Terayama | |
| 4,592,355 A | 6/1986 | Antebi | |
| 4,708,140 A | 11/1987 | Baron | |
| 4,800,879 A | 1/1989 | Golyakhovsky et al. | |
| 4,815,466 A | 3/1989 | Perlin | |
| 5,015,249 A | 5/1991 | Nakao et al. | |
| 5,026,379 A * | 6/1991 | Yoon ............................ | 606/141 |
| 5,100,418 A | 3/1992 | Yoon et al. | |
| 5,123,906 A | 6/1992 | Kelman | |
| 5,156,609 A | 10/1992 | Nakao et al. | |
| 5,171,233 A | 12/1992 | Amplatz et al. | |
| 5,207,694 A | 5/1993 | Broome | |
| 5,258,007 A | 11/1993 | Spetzler et al. | |
| 5,290,299 A * | 3/1994 | Fain et al. ..................... | 606/142 |
| 5,304,183 A | 4/1994 | Gourlay et al. | |
| 5,336,221 A | 8/1994 | Anderson | |
| 5,417,702 A | 5/1995 | Hempel | |
| 5,474,570 A | 12/1995 | Kockerling et al. | |
| 5,720,754 A | 2/1998 | Middleman et al. | |
| 5,725,532 A | 3/1998 | Shoemaker | |

(Continued)

FOREIGN PATENT DOCUMENTS

EP      1 491 153       12/2004

OTHER PUBLICATIONS

Co-owned U.S. Appl. No. 11/737,136, filed Apr. 18, 2007.

(Continued)

*Primary Examiner* — Corrine M McDermott
*Assistant Examiner* — Christina Lauer
(74) *Attorney, Agent, or Firm* — David S. Alavi

(57) ABSTRACT

A method for occluding an anatomical structure (such as a vessel or duct) having a lumen comprises: introducing percutaneously into the body of the patient a delivery device; advancing the delivery device to an occlusion site outside the lumen of an anatomical structure; deploying an occlusion instrument from the delivery device; and occluding the anatomical structure with the occlusion instrument. The advance of the delivery device and the deployment of the occlusion instrument are guided by near-real-time imaging of a target region of a body of a patient, the target region including the occlusion site on the anatomical structure. The delivery device is guided to the occlusion site outside the lumen of the anatomical structure, and the structure is occluded with the deployed occlusion instrument engaging the exterior of the structure.

4 Claims, 23 Drawing Sheets

U.S. PATENT DOCUMENTS

| | | | |
|---|---|---|---|
| 5,725,534 | A | 3/1998 | Rasmussen |
| 5,766,189 | A | 6/1998 | Matsuno |
| 5,776,062 | A | 7/1998 | Nields |
| 5,782,747 | A | 7/1998 | Zimmon |
| 5,782,839 | A | 7/1998 | Hart et al. |
| 5,810,847 | A | 9/1998 | Laufer et al. |
| 5,843,101 | A | 12/1998 | Fry |
| 5,921,996 | A | 7/1999 | Sherman |
| 5,938,667 | A | 8/1999 | Peyser et al. |
| 5,944,729 | A | 8/1999 | Blake |
| 6,004,330 | A | 12/1999 | Middleman et al. |
| 6,019,724 | A | 2/2000 | Gronningsaeter et al. |
| 6,048,331 | A | 4/2000 | Tsugita |
| 6,071,292 | A * | 6/2000 | Makower et al. ............. 606/158 |
| 6,113,611 | A | 9/2000 | Allen et al. |
| 6,139,555 | A | 10/2000 | Hart et al. |
| 6,178,968 | B1 | 1/2001 | Louw et al. |
| 6,210,418 | B1 | 4/2001 | Storz et al. |
| 6,241,740 | B1 | 6/2001 | Davis et al. |
| 6,368,338 | B1 | 4/2002 | Konya et al. |
| 6,514,265 | B2 | 2/2003 | Ho et al. |
| 6,551,332 | B1 | 4/2003 | Nguyen et al. |
| 6,607,541 | B1 | 8/2003 | Gardiner et al. |
| 6,641,593 | B1 | 11/2003 | Schaller et al. |
| 6,725,080 | B2 | 4/2004 | Melkent et al. |
| 6,726,682 | B2 | 4/2004 | Harrington et al. |
| 6,793,664 | B2 | 9/2004 | Mazzocchi et al. |
| 6,808,491 | B2 | 10/2004 | Kortenbach et al. |
| 6,853,856 | B2 | 2/2005 | Yanof et al. |
| 6,887,240 | B1 | 5/2005 | Lands et al. |
| 6,960,210 | B2 | 11/2005 | Lands et al. |
| 6,960,221 | B2 | 11/2005 | Ho et al. |
| 6,991,634 | B2 | 1/2006 | Sugiyama et al. |
| 7,094,245 | B2 | 8/2006 | Adams et al. |
| 7,452,327 | B2 | 11/2008 | Durgin et al. |
| 7,488,335 | B2 | 2/2009 | Sgro |
| 7,494,461 | B2 | 2/2009 | Wells et al. |
| 7,547,313 | B2 | 6/2009 | Gardiner et al. |
| 7,582,086 | B2 | 9/2009 | Privitera et al. |
| 2002/0115996 | A1 | 8/2002 | Wilson et al. |
| 2002/0124853 | A1 | 9/2002 | Burbank et al. |
| 2002/0169473 | A1 | 11/2002 | Sepetka et al. |
| 2002/0177861 | A1 | 11/2002 | Sugiyama et al. |
| 2002/0193823 | A1 | 12/2002 | Wallace et al. |
| 2002/0198541 | A1 | 12/2002 | Smith et al. |
| 2003/0120286 | A1 * | 6/2003 | Burbank et al. ............. 606/142 |
| 2003/0191391 | A1 | 10/2003 | Burbank et al. |
| 2003/0216772 | A1 | 11/2003 | Konya et al. |
| 2004/0044352 | A1 | 3/2004 | Fowler et al. |
| 2004/0054375 | A1 | 3/2004 | Houser et al. |
| 2004/0092978 | A1 | 5/2004 | Surti |
| 2004/0215132 | A1 | 10/2004 | Yoon |
| 2005/0033312 | A1 | 2/2005 | Suzuki |
| 2005/0049633 | A1 | 3/2005 | Watanabe |
| 2005/0113634 | A1 | 5/2005 | Burbank et al. |
| 2005/0149063 | A1 | 7/2005 | Young et al. |
| 2005/0171560 | A1 | 8/2005 | Hughett |
| 2005/0228443 | A1 | 10/2005 | Yassinzadeh |
| 2006/0047308 | A1 | 3/2006 | Ortiz et al. |
| 2007/0027466 | A1 * | 2/2007 | Ortiz et al. ..................... 606/198 |
| 2007/0043349 | A1 * | 2/2007 | Swanson et al. ................. 606/41 |
| 2007/0078459 | A1 | 4/2007 | Johnson et al. |
| 2007/0179520 | A1 | 8/2007 | West |
| 2007/0191883 | A1 | 8/2007 | Lazic et al. |
| 2007/0282355 | A1 | 12/2007 | Brown et al. |

OTHER PUBLICATIONS

Co-owned U.S. Appl. No. 11/740,940, filed Apr. 27, 2007.
Co-owned U.S. Appl. No. 11/740,943, filed Apr. 27, 2007.
Co-owned U.S. Appl. No. 11/740,944, filed Apr. 27, 2007.
Co-owned U.S. Appl. No. 11/740,942, filed Apr. 27, 2007.
Co-owned U.S. Appl. No. 11/740,946, filed Apr. 27, 2007.
Co-owned U.S. Appl. No. 11/740,947, filed Apr. 27, 2007.
Chuttani et al; "Endoscopic clip application devices"; GI Endoscopy v63 n6 p746 (2006).
Office Action (restriction) dated Aug. 18, 2009 in co-owned U.S. Appl. No. 11/737,136.
Office Action dated Sep. 2, 2009 in co-owned U.S. Appl. No. 11/740,947.
Office Action dated Nov. 17, 2009 in co-owned U.S. Appl. No. 11/740,942.
Office Action dated Nov. 20, 2009 in co-owned U.S. Appl. No. 11/740,940.
Office Action dated Jan. 7, 2010 in co-owned U.S. Appl. No. 11/737,136.
U.S. Appl. No. 12/718,972, filed Mar. 6, 2010, Quinn et al.
Office Action dated Mar. 3, 2010 in co-owned U.S. Appl. No. 11/740,947.
Office action dated Aug. 23, 2010 in co-owned U.S. Appl. No. 11/737,136.
Office action dated Feb. 11, 2011 in co-owned U.S. Appl. No. 11/737,136.
Office action dated Aug. 20, 2010 in co-owned U.S. Appl. No. 11/740,940.
Office action dated Feb. 11, 2011 in co-owned U.S. Appl. No. 11/740,940.
Office action dated Feb. 28, 2011 in co-owned U.S. Appl. No. 11/740,943.
Office action dated Mar. 22, 2011 in co-owned U.S. Appl. No. 11/740,944.
Office action dated Aug. 20, 2010 in co-owned U.S. Appl. No. 11/740,942.
Office action dated Feb. 9, 2011 in co-owned U.S. Appl. No. 11/740,942.
Office action dated Jan. 4, 2011 in co-owned U.S. Appl. No. 11/740,946.
Office action dated Aug. 20, 2010 in co-owned U.S. Appl. No. 11/740,947.
Office action dated Feb. 11, 2011 in co-owned U.S. Appl. No. 11/740,947.

* cited by examiner

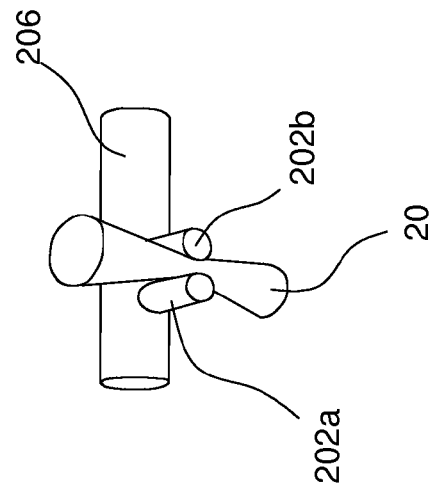
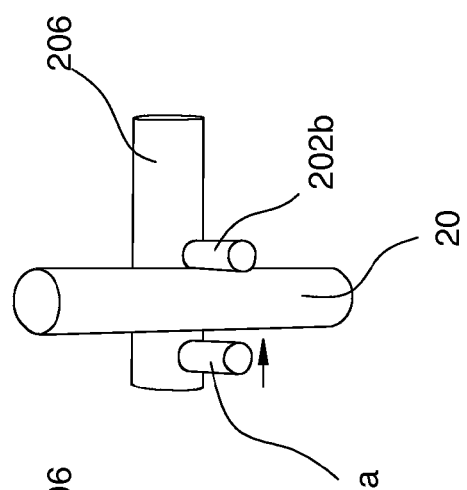
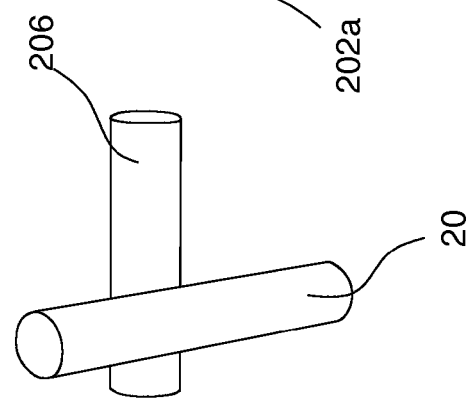
FIG. 2C
FIG. 2B
FIG. 2A

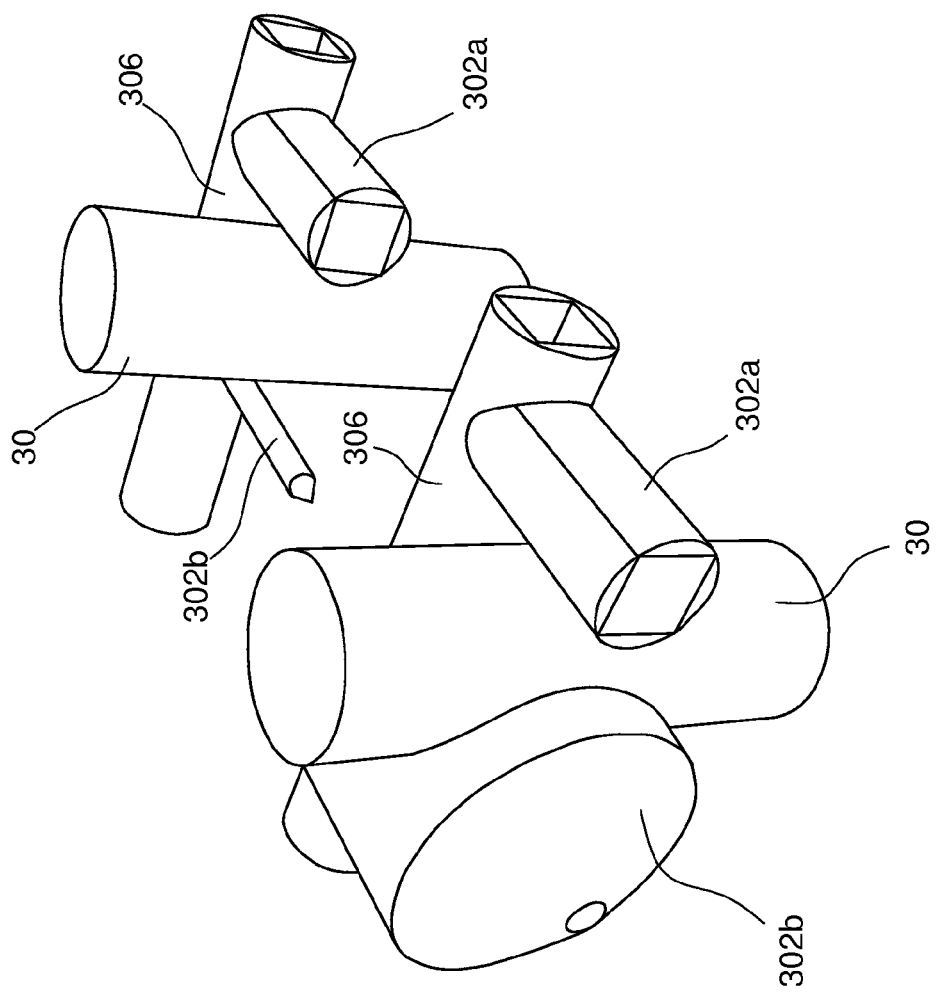

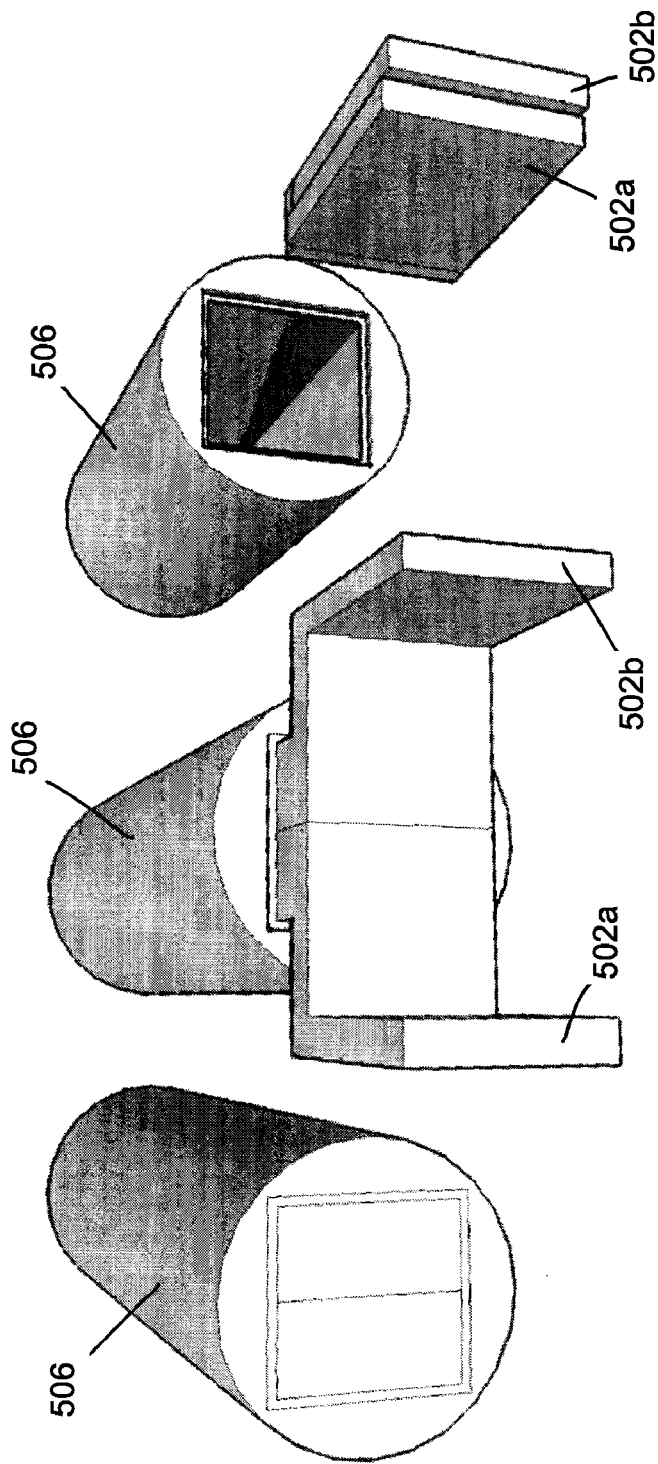

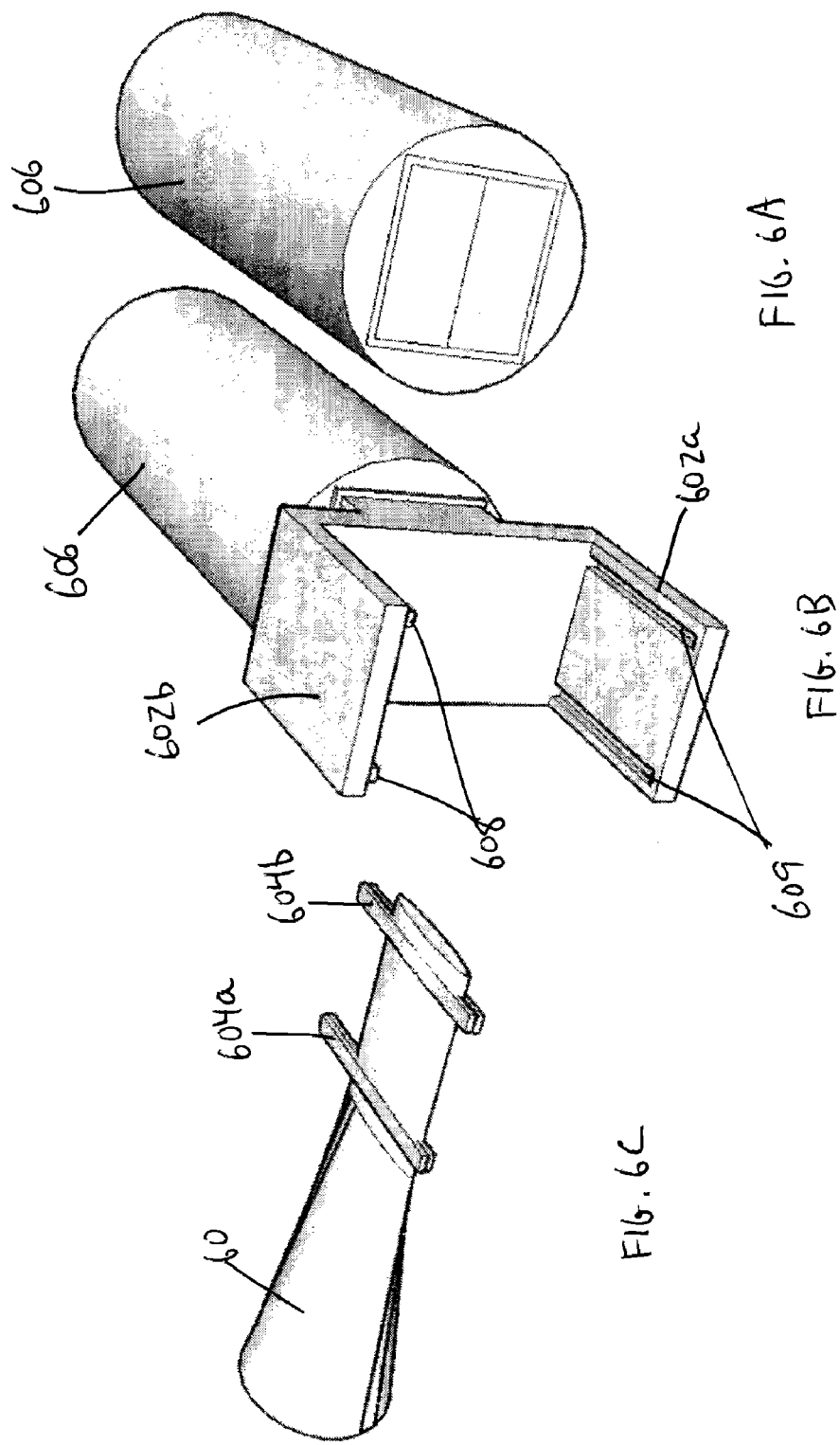

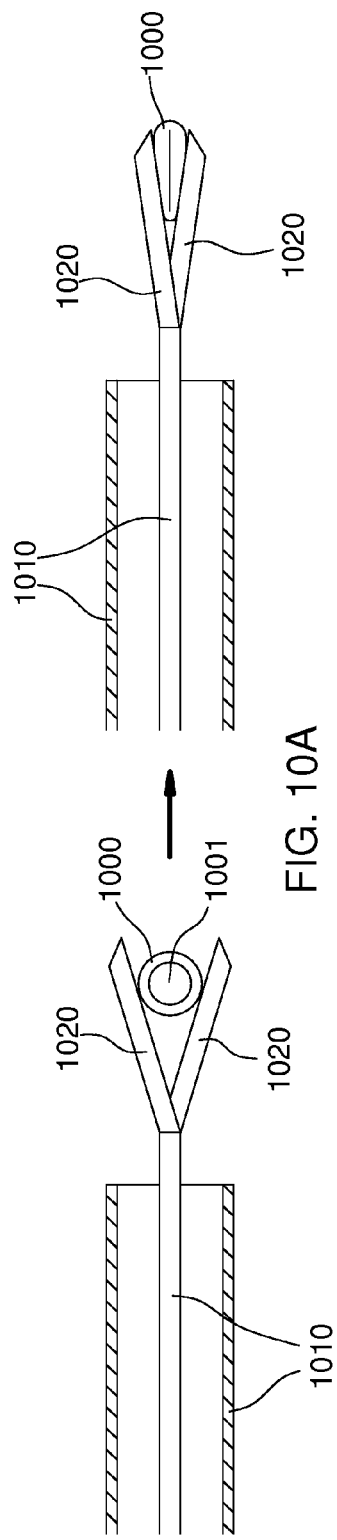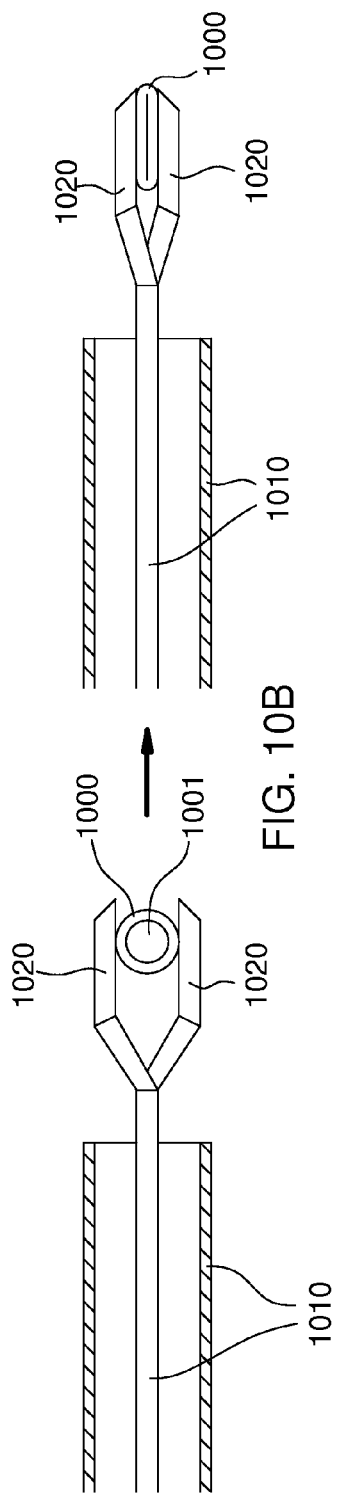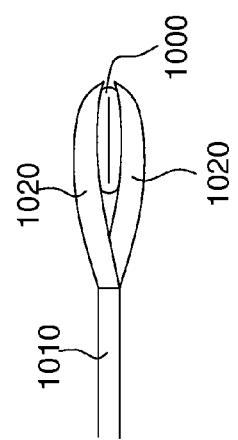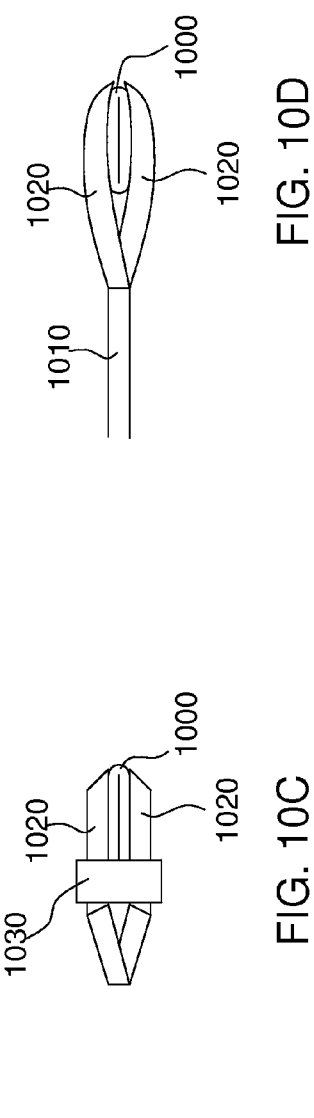

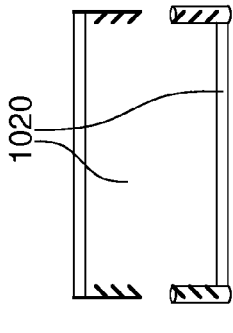
FIG. 10E
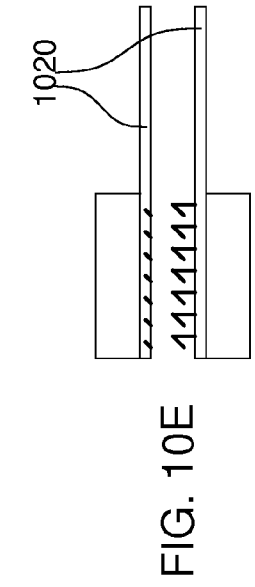
FIG. 10F
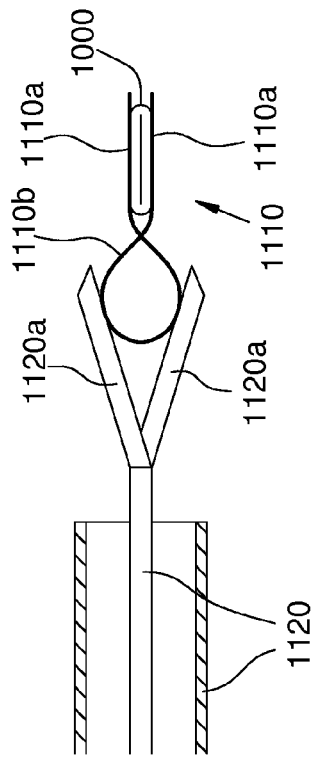
FIG. 11A
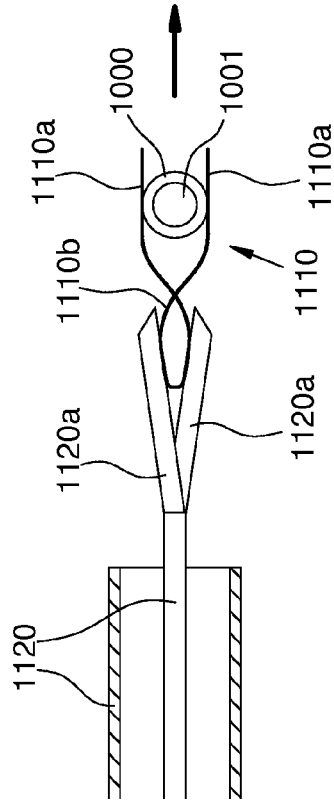
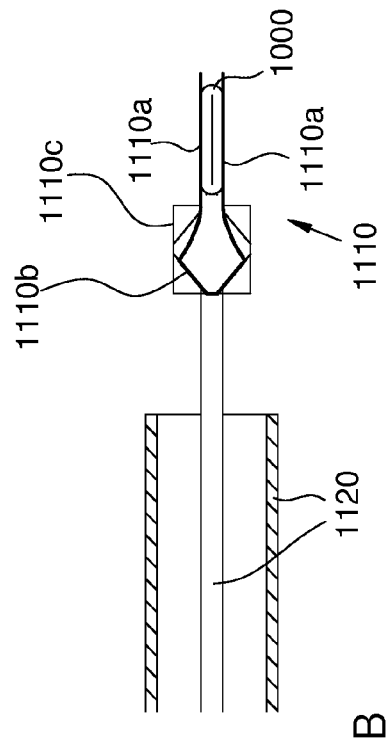
FIG. 11B
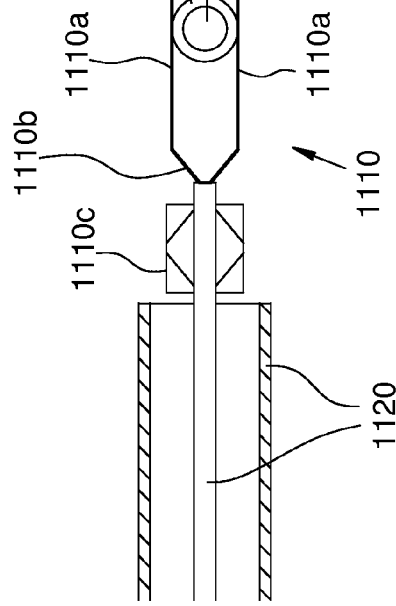

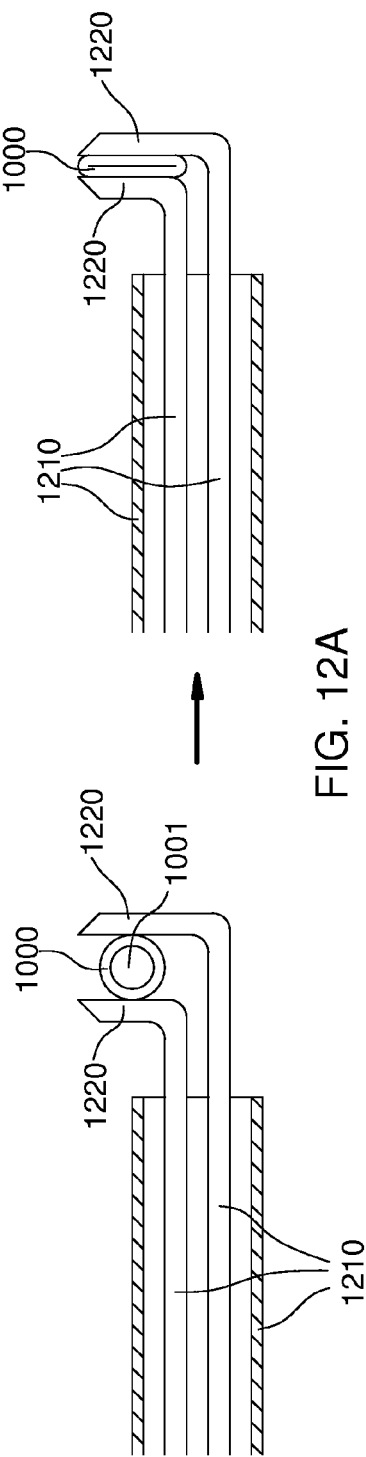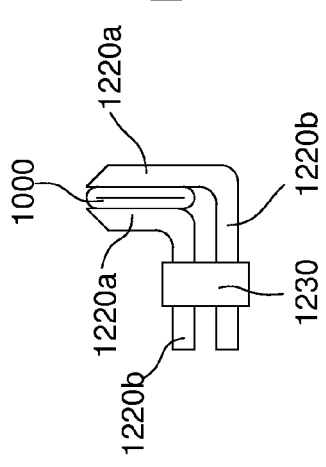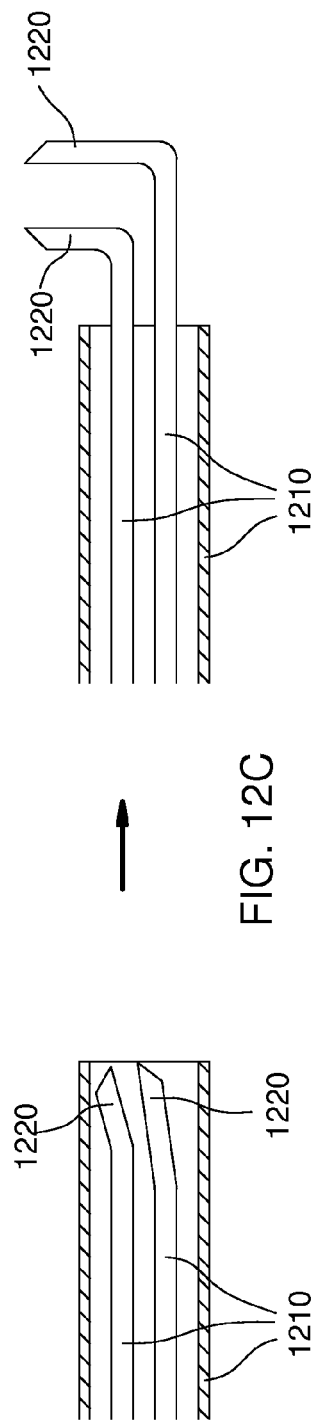
FIG. 12A
FIG. 12B
FIG. 12C

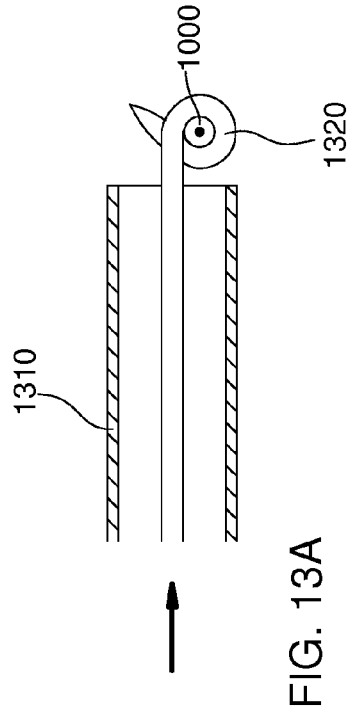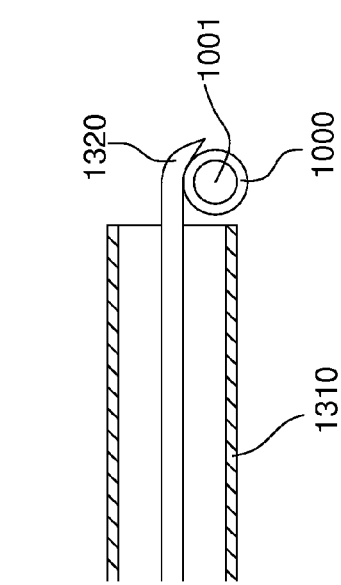
FIG. 13A
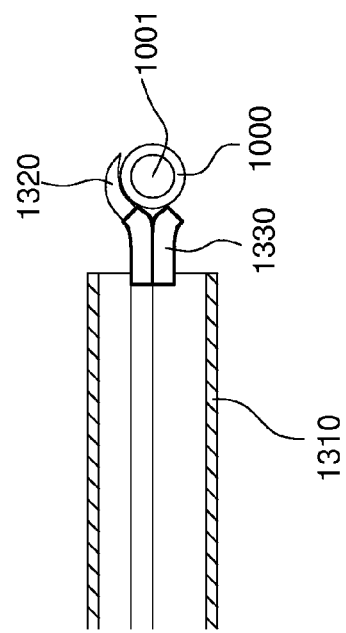
FIG. 13B

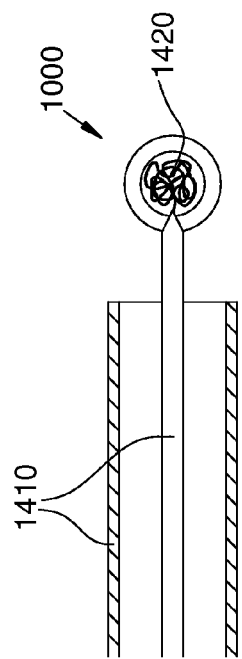
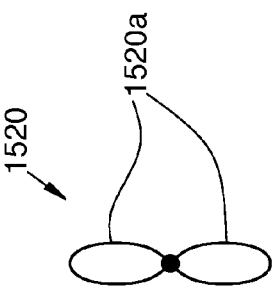
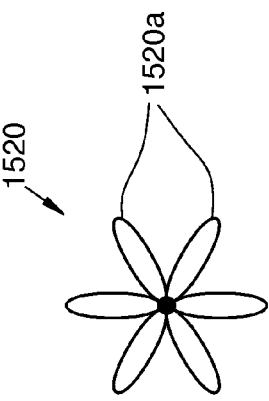
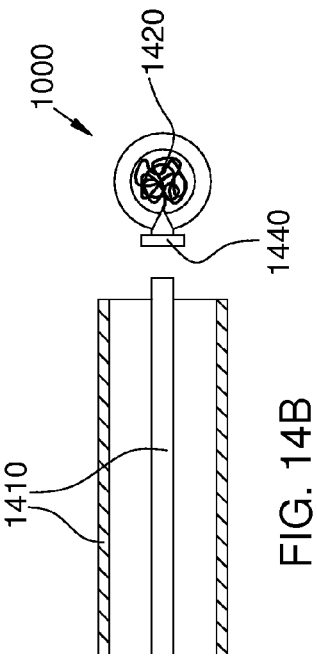
FIG. 14A
FIG. 14B
FIG. 15B
FIG. 15C

IMAGE-GUIDED EXTRALUMINAL OCCLUSION

Subject matter disclosed or claimed in this application may be related to subject matter disclosed in U.S. non-provisional application Ser. No. 11/737,136 filed Apr. 18, 2007 and U.S. provisional App. No. 60/745,080 filed Apr. 18, 2006, both of said applications being incorporated by reference as if fully disclosed herein.

BACKGROUND

The field of the present invention relates to medical or surgical procedures. In particular, apparatus and methods are described herein for image-guided, extra-luminal occlusive procedures.

Occlusion of a vascular or non-vascular anatomical structure, either temporarily or substantially permanently, may be desirable or necessary for treating a variety of medical conditions. Anatomical structures that might be occluded for therapeutic reasons or as part of a procedure may include arteries, veins, varices, aneurysms, vascular malformations, fallopian tubes, bile ducts, ureters, appendices, and so on. Some of these anatomical structures can be occluded endoluminally, i.e., from within the lumen of the structure. Endoluminal occlusions are most commonly (but not exclusively) performed on vascular structures, with the occlusion site typically being accessed by percutaneous insertion of a catheter into a vessel and which is then advanced and guided through the vascular system to the occlusion site. The catheter may typically be guided through the vessels under two-dimensional (2D) fluoroscopic imaging. Once the catheter reaches the occlusion site, the vessel may be occluded in a variety of ways, including inflation of a balloon on the tip of the catheter, or by deploying a coil, glue, a sclerosing agent, an embolization particle, or other means.

Extraluminal occlusion of an anatomical structure (i.e., occlusion from outside the structure) may be achieved in a variety of ways, including surgical clips or staples, suture ligation, cauterization techniques (e.g., a so-called harmonic scalpel), clamps or hemostats, and so on. Extraluminal occlusion is typically performed with visualization of the structure to be exposed, either direct visualization via surgical exposure of the structure or laparoscopic visualization.

SUMMARY

A method for occluding an anatomical structure (such as a vessel or duct) having a lumen comprises: introducing percutaneously into the body of the patient a delivery device; advancing the delivery device to an occlusion site outside the lumen of an anatomical structure; deploying an occlusion instrument from the delivery device; and occluding the anatomical structure with the occlusion instrument. The advance of the delivery device and the deployment of the occlusion instrument are guided by near-real-time imaging of a target region of a body of a patient, the target region including the occlusion site on the anatomical structure. The delivery device is guided to the occlusion site outside the lumen of the anatomical structure, and the anatomical structure is occluded with at least a portion of the deployed occlusion instrument engaging the exterior of the structure.

If the occlusion is intended to be substantially permanent, the method may further include detaching the engaged occlusion instrument from the delivery device, and withdrawing the delivery device from the occlusion site and from the body of the patient. If the occlusion is intended to be temporary, the method may further include disengaging the occlusion instrument from the anatomical structure and withdrawing the occlusion instrument and the delivery device from the occlusion site and from the body of the patient.

Objects and advantages pertaining to image-guided extraluminal occlusion may become apparent upon referring to the exemplary embodiments illustrated in the drawings and disclosed in the following written description or claims.

BRIEF DESCRIPTION OF THE DRAWINGS

FIGS. 2A-2C illustrate schematically another exemplary embodiment of an extraluminal occlusion instrument.

FIGS. 3A-3B illustrate schematically another exemplary embodiment of an extraluminal occlusion instrument.

FIGS. 5A-5C illustrate schematically another exemplary embodiment of an extraluminal occlusion instrument.

FIGS. 6A-6C illustrate schematically another exemplary embodiment of an extraluminal occlusion instrument.

FIGS. 10A-10F illustrate schematically another exemplary embodiment of an extraluminal occlusion instrument.

FIGS. 11A-11B illustrate schematically another exemplary embodiment of an extraluminal occlusion instrument.

FIGS. 12A-12C illustrate schematically another exemplary embodiment of an extraluminal occlusion instrument.

FIGS. 13A-13B illustrate schematically another exemplary embodiment of an extraluminal occlusion instrument.

FIGS. 14A-14B illustrate schematically another exemplary embodiment of an extraluminal occlusion instrument.

FIGS. 15A-15C illustrate schematically another exemplary embodiment of an extraluminal occlusion instrument.

Figure 1A:
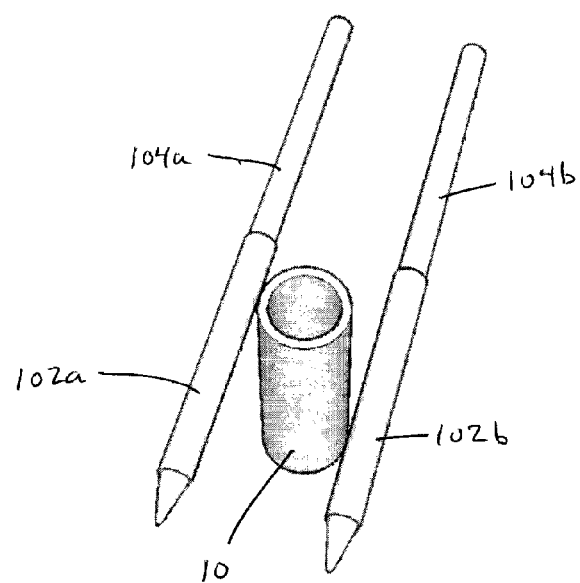
FIGS. 1A-1B illustrate schematically an exemplary embodiment of an extraluminal occlusion instrument.

The embodiments shown in the Figures are exemplary, and should not be construed as limiting the scope of the present disclosure and/or appended claims. In the Figures, "longitudinally" shall designate a direction along an elongated, tubular delivery device (a catheter, cannula, needle, etc.), while "transversely" shall denote a direction substantially perpendicular to such a delivery device. Since it may be the case that a delivery device may bend or be curved, the "longitudinal" and "transverse" directions shall be defined locally. Relative sizes or proportions of structures shown in the drawings may be distorted for clarity. For example, in many of the figures the transverse dimension is exaggerated relative to the longitudinal dimension.

DETAILED DESCRIPTION OF EMBODIMENTS

It is desirable to enable extraluminal occlusion, either temporary or permanent, of anatomical structures such as vessels, tubes, or ducts without visualization by surgical exposure or laparoscopy. Such extraluminal occlusion is typically guided by 2D or 3D imagery. Apparatus and methods for extraluminal occlusion of anatomical are disclosed hereinbelow.

In general, image-guided extraluminal occlusion is achieved by introducing an occlusion instrument into the patient's body percutaneously, using a needle, cannula, catheter, or similar elongated, tubular delivery device. The occlusion instrument and delivery device are advanced and guided by an operator through the patient's body to the occlusion site, with the operator's actions guided by near-real-time imaging of the patient's body and the delivery device (as opposed to direct visualization via surgical exposure or via laparoscope, endoscope, arthroscope, or other fiber-optic-based instrument). The term "near-real-time" is intended to encompass any imaging system that responds sufficiently rapidly so as to enable an operator to manipulate objects viewed using the imaging system. Manual or robotic manipulation may be employed for guiding the occlusion instrument and delivery device. Advancement of the delivery device and occlusion instrument to the occlusion site typically requires a wound or incision for percutaneous introduction and at least some degree of tissue spreading, dissection, or other disruption as the delivery device is advanced to the desired site. Such tissue spreading can be achieved in any suitable way, for example, using retractors, sharp or blunt probes, forceps, scissors, scalpels, water jets, gas injection, ultrasound, cautery, sutures or suture needles, clips, staples, or other implements, deployed from the delivery device or from another catheter, cannula, needle, or similar hardware introduced into the patient's body.

At least a portion of the occlusion instrument or the delivery device includes material suitable for or compatible with the imaging technique employed (e.g., radiopaque for fluoroscopy or CT, echogenic for ultrasound, non-magnetic for MRI, tracking coils for electromagnetic tracking, and so on). It may be desirable to employ in the occlusion instrument or the delivery device multiple materials having differing imaging densities (relative to the particular imaging technique employed) so as to enhance contrast or image quality, or to reduce interference or obscuration of anatomical structures near the occlusion instrument or delivery device. For example, if the delivery device is too radiopaque, it may obscure surrounding anatomical structures under fluoroscopic imaging. This can be reduced by fabricating the delivery device mostly from non-radiopaque material (e.g., some types of plastic) while including one or more radiopaque markers on the delivery device. Other arrangements can be employed.

Once at the occlusion site, the occlusion instrument is deployed, actuated, or otherwise activated to occlude the structure. If the occlusion is intended to be temporary, the occlusion instrument is left in place until occlusion of the structure is no longer required, and then disengaged from the occluded structure and withdrawn from the patient's body. If the occlusion is intended to be substantially permanent, then a portion of the occlusion instrument is typically left behind to maintain the occlusion, while the remainder of the instrument is disengaged and withdrawn from the patient's body.

Either or both of 2D or 3D imaging techniques may be employed for guiding the device to the occlusion site. 2D imaging is typically sufficient for endoluminal guiding of a catheter, since the lumen provides some degree of guidance for the advancing device. With such luminal guidance being absent from an extraluminal approach, 3D imaging may be preferred for enabling accurate positioning of the occlusion instrument in proximity to the anatomical structure to be occluded. Any suitable near-real-time imaging technique may be employed, including fluoroscopy, ultrasound, computed tomography (CT), magnetic resonance imaging (MRI), electromagnetic tracking, optical tracking, and so on. Two or more 2D images may be employed together for providing the equivalent of a 3D image, or an image inherently 3D may be employed. Recent development of CT and MRI instruments with relatively rapid scan times and improved spatial resolution enables accurate placement of the occlusion instrument near the structure to be occluded without the dissection and retraction required for direct surgical or fiber-optic visualization of the occlusion site. For each of the exemplary embodiments of occlusion instruments or delivery devices disclosed herein, any suitable imaging technique or combination of techniques may be employed for guiding the instrument to the occlusion site and properly positioning it relative to the structure to be occluded.

Temporary occlusions can be employed for transiently occluding an anatomical structure. Such might be desirable in a variety of circumstances. Examples may include temporary occlusion of arteries or veins during creation of an anastomosis, temporary occlusion of an artery to prevent distal embolization, temporary occlusion of an artery to control bleeding during trauma or surgery, and so forth. A permanent occlusion might be desirable under a variety of other circumstances. Examples may include isolation of an aneurysm or other vascular malformation, occlusion of a patent ductus arteriosus, occlusion of the cystic duct, occlusion of fallopian tubes, and so on. Other circumstances wherein temporary or permanent occlusion of an anatomical structure is necessary or desirable shall fall within the scope of the present disclosure of appended claims.

Extraluminal image-guided occlusions disclosed herein may be employed as a substitute for endoluminal procedures or for surgical or fiber-optic (e.g., laparoscopic) procedures, or may be used in conjunction with such procedures, as appropriate.

Figure 1B:
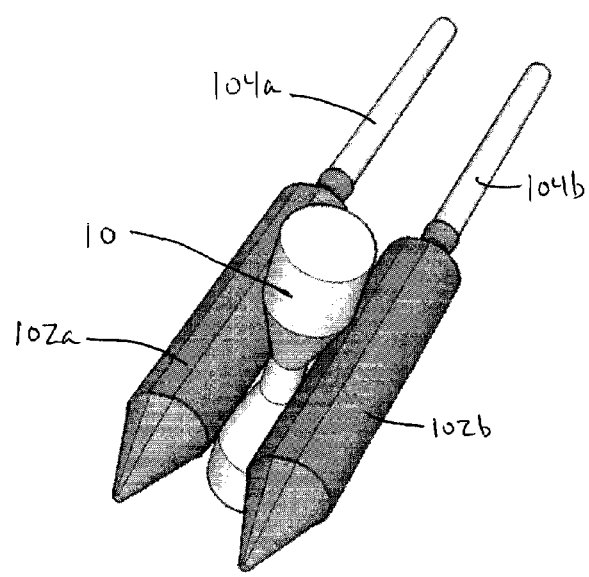

In an exemplary embodiment schematically illustrated in FIGS. 1A-1B, the occlusion instrument comprises a pair of inflatable balloons 102a and 102b each disposed on a corresponding catheter, needle, or cannula 104a or 104b. The needles 104a/104b are positioned with balloons 102a/102b on opposing sides of vessel 10 (as shown in FIG. 1A), and then the balloons are inflated (as shown in FIG. 1B). Inflation of balloons 102a/102b causes the vessel 10 to be compressed between them, occluding the vessel if it is sufficiently compressed. To compress vessel 10, needles 102a/102b must be held substantially rigidly at a fixed separation; otherwise the inflation of the balloons 102a/102b would merely push the needles 104a/104b apart. The needles 104a/104b can be introduced through the patient's skin and guided to the occlusion site within a larger needle, cannula, catheter, or other delivery device (not shown) under image-guidance (as described hereinabove). Upon reaching the occlusion site, the portions of needles 104a/104b with the balloons 102a/102b thereon are extended from the delivery device and positioned under image-guidance on opposing sides of the vessel 10. The needles 104a/104b may be held in place during inflation of balloons 102a/102b by the delivery device, or they may be provided with an additional bracket or other alignment member for keeping them substantially rigidly positioned at a fixed separation form one another. When occlusion of the vessel 10 is no longer needed or no longer desired, the balloons 102a/102b are deflated, allowing vessel 10 to return to its patent state. The needles 104a/104b with balloons 102a/102b are then withdrawn from the occlusion site and from the patient's body. Use of this exemplary embodiment has been described for occluding a vessel, however, it (and any other exemplary embodiment disclosed herein) may be used for occluding a vessel or any other anatomical structures, as described elsewhere herein. Any description of the use of any given embodiment for occluding a specific anatomical structure is given for concreteness only, and is not intended to limit the description of the particular embodiment unless specifically stated.

In another exemplary embodiment illustrated schematically in FIGS. 2A-2C, the occlusion instrument comprises a pair of clamp members 202a and 202b disposed on the side of a catheter, cannula, or other delivery device 206. Clamp members 202a/202b are held in a retracted arrangement within delivery device 206 as the occlusion instrument is introduced through the patient's skin and maneuvered under image guidance to the occlusion site and positioned relative to duct 20 (as shown in FIG. 2A). Once in position, the clamp members 202a/202b may be deployed protruding sideways from the delivery device 206 on opposing sides of the duct 20 (as shown in FIG. 2B). The clamp members 202a/202b may protrude through an opening in the side of delivery device 206, and one or both clamp members 202a/202b is movable longitudinally along a portion of the length of delivery device 206. By moving the clamping members together with the duct 20 between them, the duct is compressed and eventually occluded when enough force is applied (as shown in FIG. 2C). The clamping members 202a/202b and the portion of delivery device 206 near the occluded duct 20 are sufficiently rigid so as to enable compression and occlusion of the duct. When the occlusion of duct 20 is no longer needed or no longer desirable, the clamp members 202a/202b are moved apart, releasing the duct 20 which returns to its patent state. The clamp members 202a/202b are withdrawn within the deliver device 206, which is then in turn withdrawn from the patient's body.

In one implementation of the embodiment of FIGS. 2A-2C, the clamping members 202a/202b may comprise resilient members formed from a suitable metal (e.g. nitinol wire) or plastic. The resilient members may be held within the delivery device 206 in a deformed shape, may spring out through an opening in delivery device 206 to assume their non-deformed shapes, may be pulled or pushed along the delivery device 206 for occluding or releasing the duct 20, and may be retracted within delivery device 206 (presumably in a deformed state again) for withdrawal from the body. In an alternative implementation of the embodiment of FIGS. 2A-2C, the clamping members 202a/202b may comprise substantially rigid members that fold or retract into the delivery device 206 and then unfold or extend out of the delivery device at the occlusion site. Many other arrangements are possible for providing the disclosed functionality, and shall fall within the scope of the present disclosure or appended claims.

FIGS. 3A-3B illustrate schematically another exemplary embodiment similar to that of FIGS. 2A-2C, with members 302a and 302b extending laterally from delivery device 306 on opposing sides of vessel 30. Instead of clamping members as in FIGS. 2A-2C, the one or both of member 302a/302b includes an inflatable balloon (member 302b in FIGS. 3A-3B). Once positioned with the members 302a/302b on opposing sides of vessel 30, the balloon is inflated to compress the vessel 30 between the members 302a/302b. The members 302a/302b and the portion of delivery device 306 supporting them are sufficiently rigid so as to enable compression and occlusion of the vessel 30 upon inflation of the balloon. When occlusion of vessel 30 is no longer needed or no longer desired, the balloon is deflated, members 302a/302b are withdrawn within the delivery device 306, which is in turn withdrawn from the patient's body.

Figure 4B:
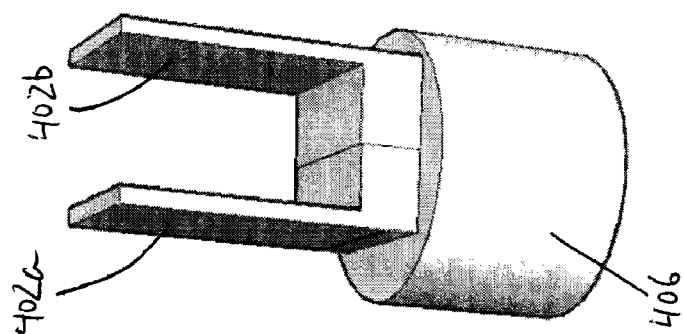
FIGS. 4A-4C illustrate schematically another exemplary embodiment of an extraluminal occlusion instrument.
Figure 4C:
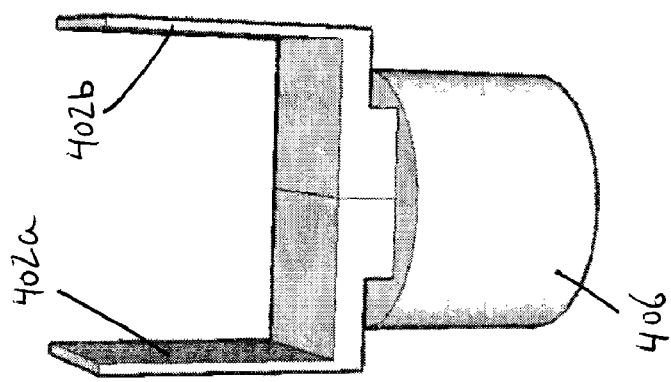
Figure 4A:
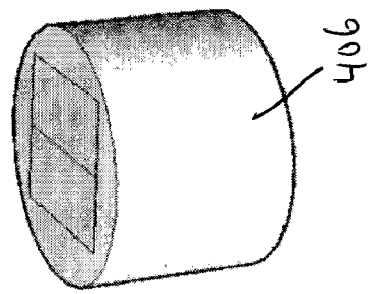

FIGS. 4A-4C illustrate schematically another exemplary embodiment comprising clamp members 402a and 402b extending longitudinally from the end of a needle, cannula, catheter, or other delivery device 406. The method of deployment and occlusion is similar to that described for the embodiment of FIGS. 2A-2C, with the clamp members 402a/402b held within the delivery device 406 (as shown in FIG. 4A) during image-guided positioning of the occlusion instrument near the duct, vessel, or other anatomical structure to be occluded (not shown in FIGS. 4A-4C). Once in place, the clamp members 402a/402b are extended out of the delivery device 406 (as shown in FIG. 4B), opened (as shown in FIG. 4C) and positioned around the anatomical structure, and urged toward one another to occlude the structure (as shown in FIG. 4B, which does not show the anatomical structure). When the occlusion is no longer needed or no longer desired, the clamp members 402a/402b are disengaged from the anatomical structure and withdrawn within the delivery device 406, which is then withdrawn from the patient's body. The clamp members 402a/402b may be configured in any way suitable for providing the necessary movements and clamping action.

A variation of the embodiment of FIGS. 4A-4C that is adapted for substantially permanently occluding a vessel, duct, or other anatomical structure is illustrated schematically in FIGS. 5A-5C (anatomical structure not shown). In this variation, the clamp members 502a and 502b are detachable. After being guided to the occlusion site in a retracted or withdrawn arrangement (FIG. 5A), extended and positioned around the anatomical structure (FIG. 5B; anatomical structure not shown), and then urged together to occlude the structure, the clamp members 502a/502b are secured together around the structure and detached from the delivery device 506 (FIG. 5C). The delivery device 506 is then withdrawn from the patient's body.

Another variation of the embodiment of FIGS. 4A-4C that is adapted for substantially permanently occluding a duct 60 is illustrated schematically in FIGS. 6A-6C (duct 60 shown only in FIG. 6C). In this variation the clamp members 602a and 602b are adapted for placing and securing clips or staples 604a and 604b on the duct 60 to substantially permanently occlude it (FIG. 6C). In this example clamp members 602a/602b include ridges 608 and grooves 609 for securing the clips 604a/604b; any other suitable structures, arrangements, or adaptations may be employed. The occlusion instrument is image-guided to the occlusion site with the clamp members 602a/602b in a withdrawn or retracted arrangement within delivery device 606 (FIG. 6A), extended and positioned around the duct 60 (FIG. 6B; duct 60 not shown), and then urged together to secure clips 604a/604b onto the duct 60 (FIG. 6C). Once the clips are secured, the clamp members 602a/602b are disengaged from the duct 60, withdrawn into the delivery device 606, and withdrawn form the patient's body.

Figures 7A, 7B:
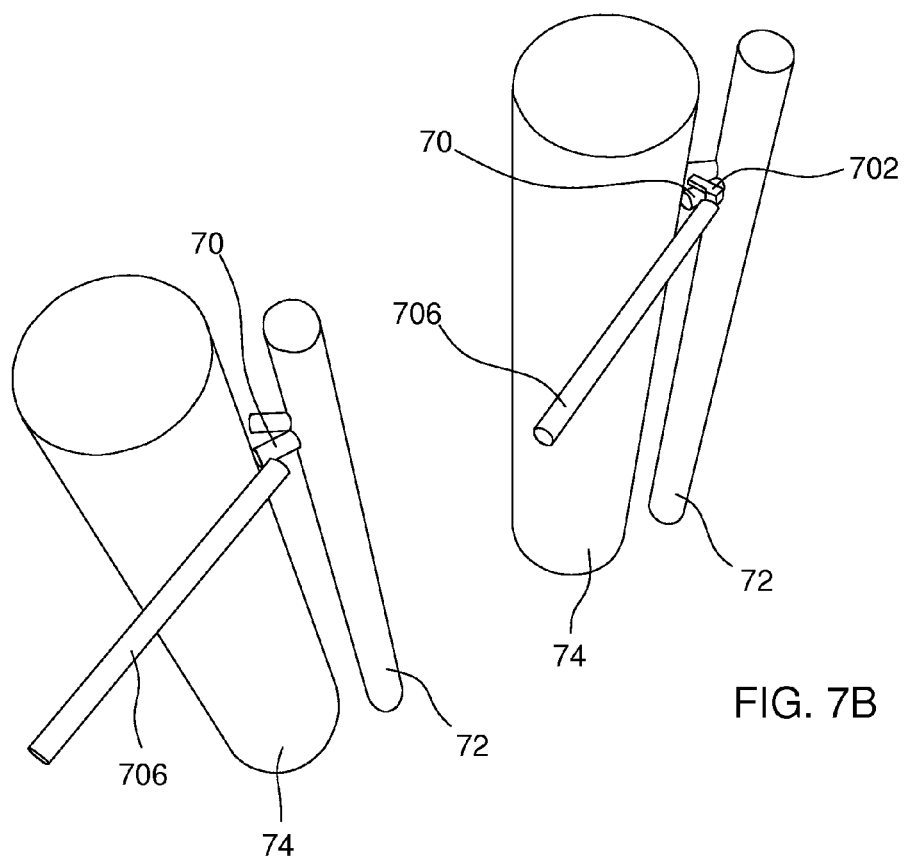
FIGS. 7A-7B illustrate schematically another exemplary embodiment of an extraluminal occlusion instrument.

The end-deployed embodiments of FIGS. 4A-4C, 5A-5C, and 6A-6C are each shown with the respective clamp members deployed longitudinally from the end of the corresponding delivery device and extending longitudinally. Each may be modified so that the clamp members may be extended laterally after longitudinal deployment from the end of the delivery device. An example of such an embodiment and its use are illustrated schematically in FIGS. 7A and 7B. The delivery device 706 is image-guided to a location near a lumbar artery 70 branching from the aorta 72 very near the spinal column 74 (as shown in FIG. 7A). Clamp members 702 are extended longitudinally from the end of the delivery device 706 and extend laterally. The clamp members 702 are positioned around the lumbar artery 70 and urged together to occlude the artery (as shown in FIG. 7B). The clamp members 702 may be disengaged and withdrawn after occluding the artery temporarily, may be detached and left in place to occlude the artery substantially permanently, or may be used to secure clips to the artery to occlude it substantially permanently. It should be noted that the side-deployed embodiments of FIGS. 2A-2C and 3A-3B could also be used in the situation depicted in FIGS. 7A-7B. The exemplary use schematically illustrated in FIGS. 7A-7B demonstrates one capability provided by the occlusion instruments disclosed herein, namely, the ability to occlude an artery, duct, or other anatomical structure in an anatomically crowded or restricted space without the need for surgical or laparoscopic dissection or retraction.

Figure 8C:
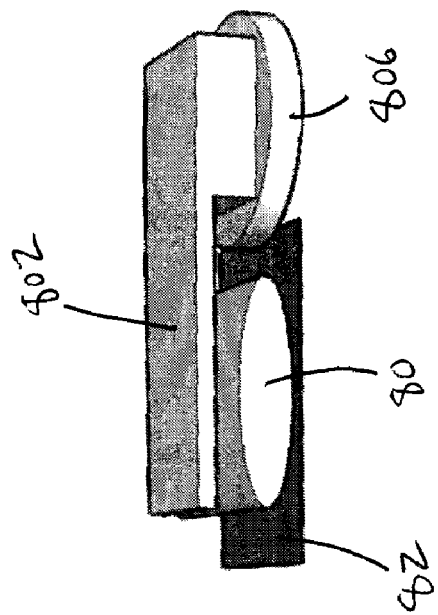
FIGS. 8A-8C illustrate schematically another exemplary embodiment of an extraluminal occlusion instrument.
Figure 8B:
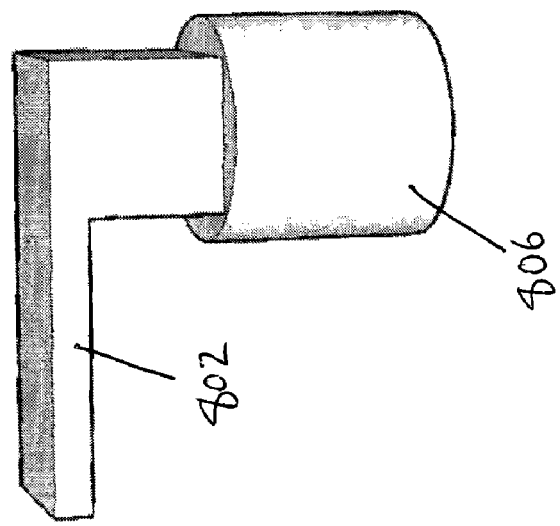
Figure 8A:
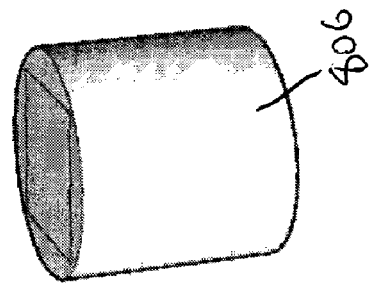

Another exemplary embodiment of an image-guided occlusion instrument is illustrated schematically in FIGS. 8A-8C. A delivery device 806 is image-guided to the occlusion site with the occlusion instrument contained within (as shown in FIG. 8A). Once at the occlusion site, a clamping member 802 is extended laterally. The clamping member 802 may be extended from the end of the delivery device before extending laterally (as shown in FIGS. 8B-8C), or may protrude laterally from the side of the delivery device 806 (not shown; similar to the embodiments of FIGS. 2A-2C and 3A-3B). Once positioned against a vessel 80 (vessel not shown in FIG. 8B), the clamping member 802 is drawn back to compress the vessel 80 against another anatomical structure 82 in the patients body, e.g., bone, tendon, ligament, skin, and so on. When occlusion of vessel 80 is no longer needed or no longer desired, the force applied by clamping member 80 may be removed, releasing the vessel 80 and allowing it to return to its patent state. The clamping member 802 is withdrawn or retracted into the delivery device 806, which is then withdrawn from the patient's body.

Figure 9A:
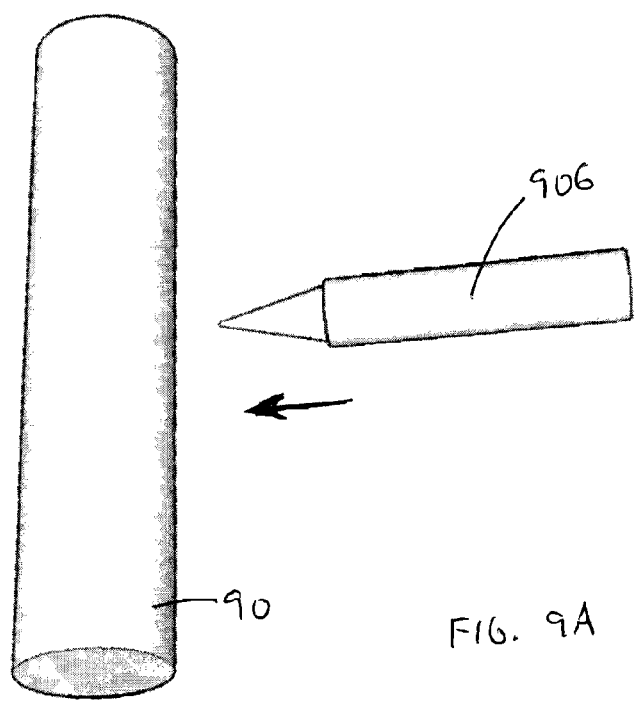
FIGS. 9A-9E illustrate schematically another exemplary embodiment of an extraluminal occlusion instrument.
Figure 9B:
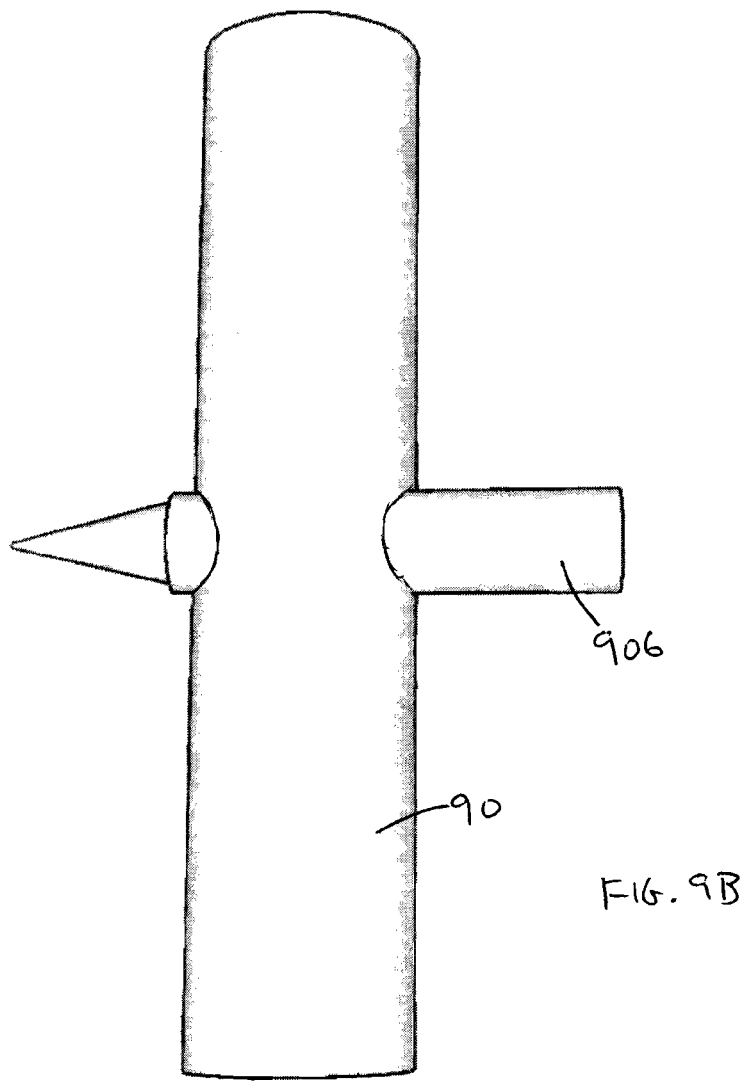
Figure 9C:
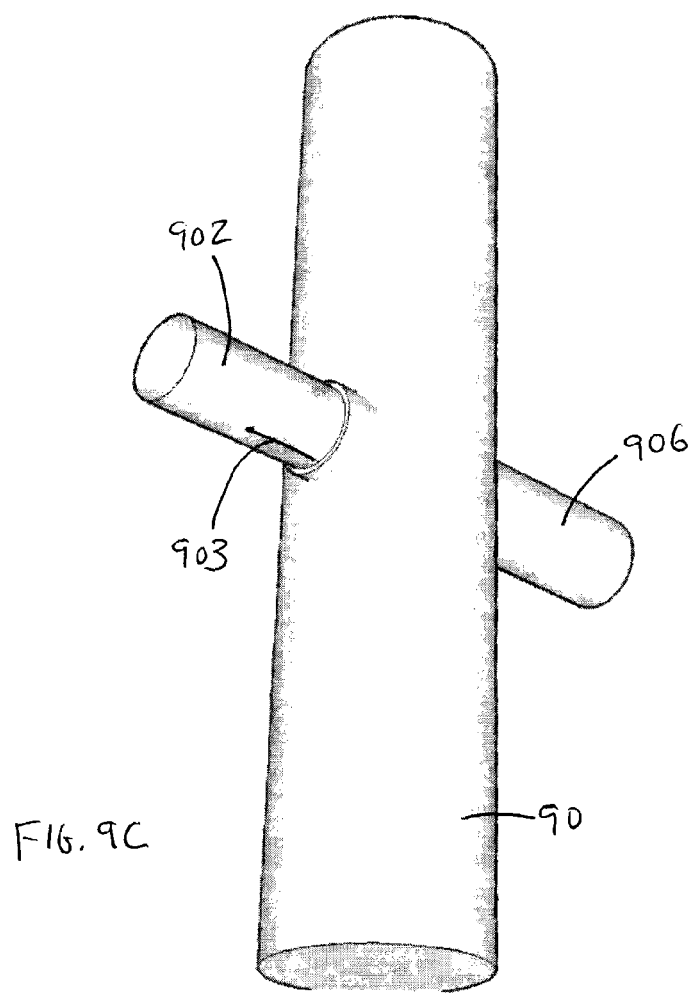
Figure 9D:
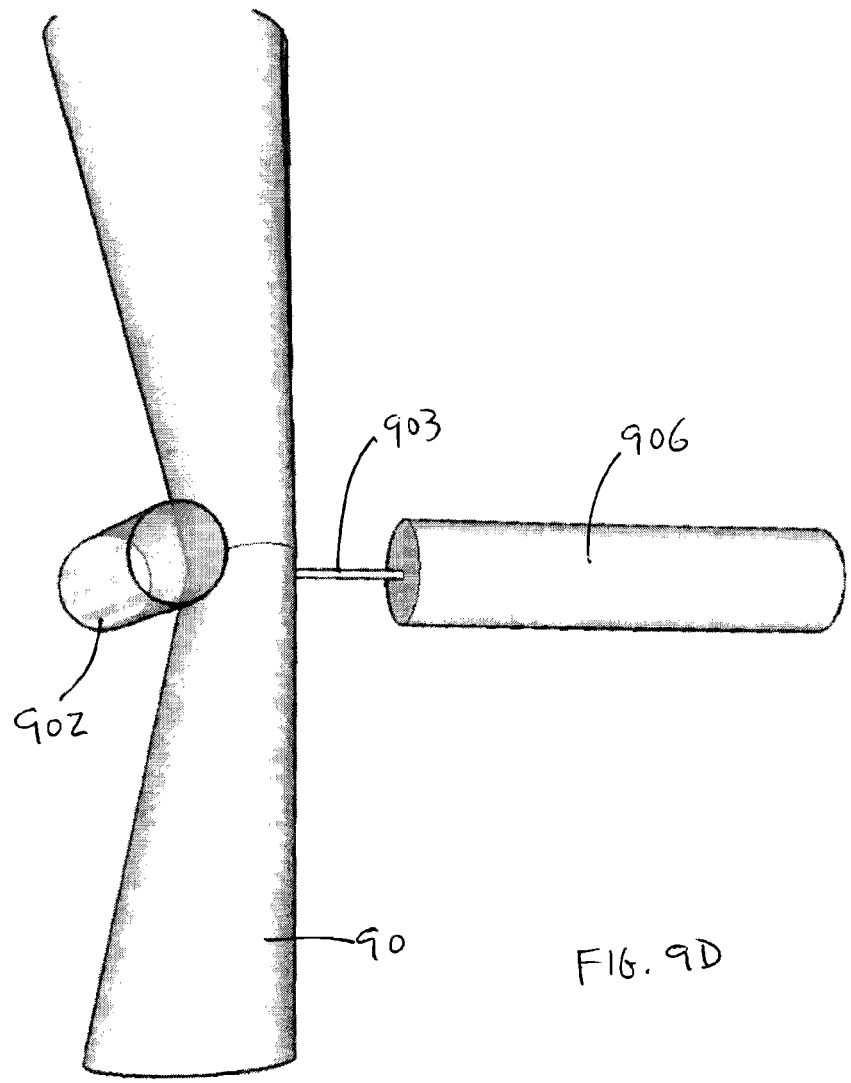
Figure 9E:
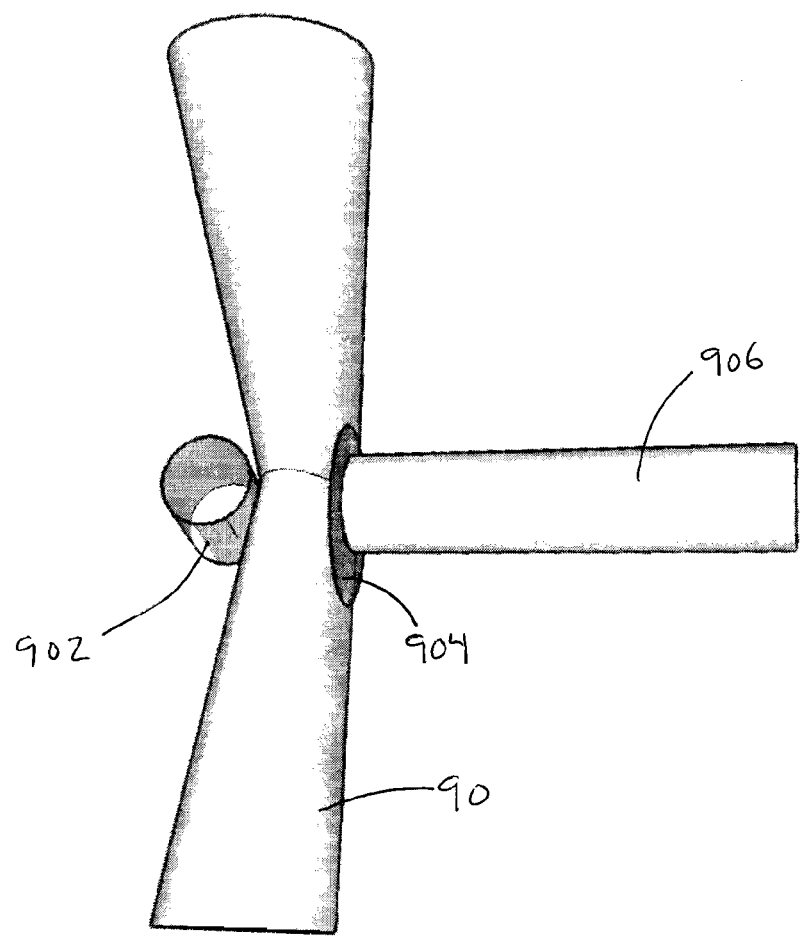

Another exemplary embodiment is illustrated schematically in FIGS. 9A-9E. A delivery device 906 is advanced under image-guidance to an occlusion site on vessel 90 (FIG. 9A). Delivery device 906 may comprise a needle, cannula, catheter, or other suitable delivery device, and includes a tip adapted for piercing the vessel 90. Still under image-guidance, the operator advances the delivery device 906, pierces vessel 90, and passes the delivery device 906 through the vessel 90 (FIG. 9B). Once through the vessel, a clamp member 902 is advanced along the delivery device 906 and passed through the vessel 90 (FIG. 9C). Once through the vessel 90, the clamp member is released from the delivery device 906 except for a cable or tether 903, and delivery device 906 is withdrawn from vessel 90 (FIG. 9D). A retainer 904 is advanced along tether 903 so that the vessel 90 is compressed between the clamp member 902 and the retainer 904, occluding the vessel (FIG. 9E). The retainer 904 is secured to the tether 903, which is then released from the delivery device 906. The delivery device is withdrawn from the occlusion site and from the patient's body, leaving the vessel occluded by compression between clamp member 902 and retainer 904 held together by tether 903. The embodiment of FIGS. 9A-9E might be best suited for achieving substantially permanent occlusion of vessel 90.

The exemplary embodiments described herein and equivalents and variations thereof, positioned and deployed under near-real-time image-guidance, may be employed for occluding a variety of anatomical structures in a variety of clinical situations. The following are exemplary only, and not intended to comprise an exhaustive list.

Image-guided extraluminal occlusion may be employed for substantially permanently occluding blood vessels for treating various conditions, including varicocele, varicose veins, Type II endoleaks of a lumber artery or inferior mesenteric artery, pelvic congestion, uterine artery, patent ductus arteriosus (PDA), arterio-venous malformation (AVF), epistaxis, intracranial aneurysm, visceral bleeding (including spleen or GI tract). Image-guided extraluminal occlusion may be employed for temporarily occluding blood vessels in a variety of clinical settings, including occlusion of a carotid artery, occlusion of the aorta during trauma treatment, or occlusion of any vessel during a vascular procedure (such as installation of a stent graft or performance of a bypass procedure). Imaged-guided extraluminal occlusion may be employed for performing tubal ligation. Image-guided extraluminal occlusion may be employed during an organ-removal procedure, including removal of gall bladder, adrenal gland, kidney, spleen, lung, appendix, and so on. During such an organ removal procedure, image-guided extraluminal occlusion might be employed for occluding one or more blood vessels supplying the organ, or for occluding one or more ducts associated with the organ. Image-guided extraluminal occlusion could be employed during gastric stapling or gastric bypass surgery.

A generalized method for extraluminal occlusion of an anatomical structure having a lumen comprises: providing near-real-time imaging of a target region of a body of a patient, the target region including an occlusion site on the anatomical structure; introducing percutaneously into the body of the patient a delivery device; under guidance of the imaging, advancing the delivery device to an occlusion site outside the lumen of the anatomical structure; under guidance of the imaging, deploying an occlusion instrument from the delivery device; and occluding the anatomical structure with the deployed occlusion instrument engaging the anatomical structure.

If the occlusion of the anatomical structure is intended to be temporary, then the method further comprises disengaging the occlusion instrument from the anatomical structure and withdrawing the occlusion instrument and the delivery device from the body of the patient. If the occlusion is intended to be substantially permanent, the method further comprises detaching the engaged occlusion instrument from the delivery device and withdrawing the delivery device from the body of the patient while leaving the deployed occlusion instrument engaging the anatomical structure and occluding the anatomical structure. The occlusion method can further comprising cauterizing the anatomical structure at the occlusion site during or after deploying the occlusion instrument. The occlusion method can be employed to temporarily or permanently occlude any desired or indicated anatomical structure, including but not limited to a blood vessel, an aneurysm or vascular malformation, a patent ductus arteriosus, a lymph vessel, an airway, a bile duct, a pancreatic duct, a ureter, a fallopian tube, a vas deferens, or an appendix.

Exemplary embodiments of apparatus and methods for extraluminal occlusion are disclosed herein. However, the present disclosure shall not be limited to only those exemplary embodiments explicitly disclosed. Each exemplary embodiment includes a delivery device that can comprise a catheter, cannula, needle, or other suitable elongated, tubular structure, and can also include other hardware (wires, rods, tethers, handles, actuators, and so forth) for advancing, deploying, or retracting an occlusion instrument or other instruments, implements, or objects therethrough, such as probes, retractors, forceps, scissors, scalpels, cauterizers, sutures or suture needles, clips, staples, and so forth. The delivery device can be advanced directly through the patient's body, alone or alongside another catheter, cannula, or other tubular device. Alternatively, the delivery device can be advanced through another catheter, cannula, or other tubular device.

In FIGS. 10A and 10B are illustrated schematically exemplary apparatus and methods for occluding an anatomical structure having a lumen (similar to those illustrated in FIGS. 4A-4C and 5A-5C). The method comprises: providing near-real-time imaging of a target region of a body of a patient, the target region including an occlusion site on the anatomical structure; introducing percutaneously into the body of the patient an elongated, tubular delivery device 1010; under guidance of the imaging, advancing the delivery device 1010 to an occlusion site outside the lumen 1001 of the anatomical structure 1000; under guidance of the imaging, advancing a pair of longitudinally-extending clamping jaws 1020 through the leading end of the delivery device 1010 so that the anatomical structure 1000 is positioned between the clamping jaws 1020; and urging the clamping jaws 1020 toward one another transversely with the anatomical structure 1000 between them, thereby engaging the exterior of the anatomical structure and occluding the it.

The longitudinally-extending clamping jaws 1020 and the delivery device 1010 can each comprise any suitable material or combination of materials. Metals, plastics, or polymers of various types are often employed for fabricating medical devices, and can be employed for forming any of the devices disclosed herein. In exemplary embodiments in which a member or component is deformed or altered in shape, in some instances it can be desirable to employ so-called "shape-memory" alloys such as copper-zinc-aluminum alloys, copper-aluminum-nickel alloys, or nickel-titanium alloys (e.g., Nitinol or MP35N).

If the occlusion is temporary, then the clamping jaws 1020 can be disengaged from the anatomical structure 1000 and the clamping jaws 1020 and the delivery device 1010 can be withdrawn from the body of the patient. If the occlusion is intended to be substantially permanent, then the clamping jaws 1020 can be detached from the delivery device 1010 and left engaging the anatomical structure 1000 and occluding it when the delivery device 1010 is withdrawn from the occlusion site and the patient's body.

FIG. 10C illustrates schematically a retaining ring 1030 advanced over a portion of the longitudinally-extending clamping jaws 1020 so as to retain the clamping jaws engaged with the anatomical structure 1000. The ring 1030 can comprise (i) a threaded ring engaged with mating threads on the clamping jaws, (ii) a slip ring adapted to slide over the clamping jaws and to be held in place by friction or adhesive, or (iii) a snap ring adapted to engage a flange, tang, ratchet, or groove on the clamping jaws.

The longitudinally-extending clamping jaws 1020 can be secured to the delivery device 1010 in a variety of ways that enable detachment of the clamping jaws 1020 from the delivery device 1010. Examples of suitable attachments can include, but are not limited to: (i) a threaded fastener, with the clamping jaws 1020 detached from the delivery device 1010 by unscrewing the threaded fastener: (ii) a detent mechanism, with the clamping jaws detached from the delivery device by disengaging the detent mechanism; (iii) a tether, with the clamping jaws 1020 detached from the delivery device by separating the tether from the clamping jaws 1020 (e.g., by cutting; in this example the delivery device 1010 can further include a blade arranged to advance through the delivery device 1010 to cut the tether); (iv) a retractable pin, with the clamping jaws 1020 detached from the delivery device 1010 by retracting the pin.

The clamping jaws 1020 or the delivery device 1010 can be used to cauterize (e.g., by electro-cautery) the anatomical structure at the occlusion site during or after engaging the clamping jaws. Alternatively, a separate cauterizer can be introduced to the occlusion site, either through delivery device 1010 or through an independent delivery device.

FIG. 10A shows substantially straight clamping jaws 1020 that are hinged so that the angle between them changes as they are opened and closed. FIG. 10B shows straight clamping jaws 1020 that remain substantially parallel to one another as they are opened and closed. If needed of desired, curved clamping jaws can be employed (FIG. 10D). FIGS. 10E and 10F show pairs of clamping jaws 1020 that comprise a pair of mechanically discrete members arranged to engage one another with the anatomical structure 1000 between them, employing any suitable mechanism such as a linear ratchet, groove, flange, tang, or similar mechanism.

FIGS. 11A and 11B illustrate schematically another exemplary apparatus and method for occluding an anatomical structure. The method comprises: providing near-real-time imaging of a target region of a body of a patient, the target region including an occlusion site on the anatomical structure 1000; introducing percutaneously into the body of the patient an elongated, tubular delivery device 1120; under guidance of the imaging, advancing the delivery device 1120 to an occlusion site outside the lumen 1001 of the anatomical structure 1000; under guidance of the imaging, advancing a deformable clamp 1110 having opposing clamp jaws 1110*a* through the leading end of the delivery device 1120 with the clamp jaws 1110*a* in an open position so that the anatomical structure 1000 lies between them; and deploying the clamp 1110 with the clamp jaws 1110*a* biased toward one another with the anatomical structure between them, thereby engaging the exterior of the anatomical structure 1000 and occluding it.

As with the previously described embodiments, if the occlusion is temporary, then the deformable clamp 1110 can be disengaged from the anatomical structure 1000 and the deformable clamp 1110 and the delivery device 1120 can be withdrawn from the body of the patient. If the occlusion is intended to be substantially permanent, then the deformable clamp 1110 can be detached from the delivery device 1120 and left engaging the anatomical structure 1000 and occluding it when the delivery device 1120 is withdrawn from the occlusion site and the patient's body. The deformable clamp 1110 can be secured to the delivery device in any of the ways disclosed above for enabling it to be detached from the delivery device 1120. The deformable clamp 1110 or the delivery device 1120 can be used to cauterize (e.g., by electro-cautery) the anatomical structure at the occlusion site during or after engaging the clamping jaws. Alternatively, a separate cauterizer can be introduced to the occlusion site, either through delivery device 1120 or through an independent delivery device.

In the exemplary embodiment of FIG. 11A, the clamp jaws 1110*a* are connected by a resilient member (loop 1110*b*) so that the clamp jaws 1110*a* are biased toward or past one another in the clamp's non-deformed state. To advance the deformable clamp 1110, a transverse force is applied to loop 1110*b* by the delivery device 1120 (by jaws 1120*a* in this example; any other suitable deforming member or mechanism can be employed) to deform the clamp 1110 into the open position in which the clamp jaws 1110*a* are forced apart against the bias of the resilient loop 1110*b*, thereby enabling advancement of the clamp 1110 so that the anatomical structure 1000 lies between the clamp jaws 1110*a*. To deploy the clamp 1110, the force is released and the clamp closes on the anatomical structure.

In the exemplary embodiment of FIG. 11B, the clamp jaws 1110*a* are connected by a resilient member 1110*b* so that the clamp jaws 1110*a* are biased in the open position in the clamp's non-deformed state. Once the clamp 1110 is positioned with the anatomical structure 1000 between the clamp jaws 1110*a*, a deforming member 1110*c* is placed on the clamp 1110 to force the clamp jaws 1110*a* toward one another against the bias of the resilient member 1110*b*, thereby occluding the anatomical structure 1000. The deforming member 1110*c* typically includes a hole arranged so that the deforming member 1110*c* can receive within the hole a portion of the deformable clamp 1110, thereby forcing the clamp jaws 1110*a* toward one another against the bias of the resilient member 1110*b*. The hole can include at least one detent arranged to retain a portion of the deformable clamp 1110 within the hole (e.g., the interior angled portion of the member 1110*c* in FIG. 11B that receives the angled portion of the clamp 1110 where the jaw 1110*a* meets the resilient member 1110*b*).

FIG. 12A illustrates schematically another exemplary apparatus and method for occluding an anatomical structure (similar to those illustrated in FIGS. 2A-2C and 7A-7B). The method comprises: providing near-real-time imaging of a target region of a body of a patient, the target region including an occlusion site on the anatomical structure 1000; introducing percutaneously into the body of the patient an elongated, tubular delivery device 1210; under guidance of the imaging, advancing the delivery device 1210 to an occlusion site outside the lumen of the anatomical structure 1000; under guidance of the imaging, advancing a pair of laterally-extending clamping jaws 1220 through the leading end of the delivery device so that the anatomical structure 1000 is positioned between the clamping jaws 1220; and urging the clamping jaws 1220 toward one another longitudinally with the anatomical structure 1000 between them, thereby engaging the exterior of the anatomical structure 1000 and occluding it.

As with previously described embodiments, if the occlusion is temporary, then the laterally-extending clamping jaws 1220 can be disengaged from the anatomical structure 1000 and the laterally-extending clamping jaws 1220 and the delivery device 1210 can be withdrawn from the body of the patient. If the occlusion is intended to be substantially permanent, then the laterally-extending clamping jaws 1220 can be detached from the delivery device 1210 and left engaging the anatomical structure 1000 and occluding it when the delivery device 1210 is withdrawn from the occlusion site and the patient's body. The laterally-extending clamping jaws 1220 can be secured to the delivery device 1210 in any of the ways disclosed above for enabling it to be detached from the delivery device 1210. The laterally-extending clamping jaws 1220 or the delivery device 1210 can be used to cauterize (e.g., by electro-cautery) the anatomical structure at the occlusion site during or after engaging the clamping jaws. Alternatively, a separate cauterizer can be introduced to the occlusion site, either through delivery device 1210 or through an independent delivery device.

FIG. 12B illustrates schematically each clamping jaw 1220 including a laterally-extending segment 1220*a* arranged to engage the anatomical structure 1000 and a longitudinally-extending segment 1220*b*. A retaining ring 1230 can be advanced over the longitudinally-extending segments 1220*b* of the clamping jaws 1220 so as to retain the clamping jaws 1220 engaged with the anatomical structure 1000. The ring 1230 can comprise (i) a threaded ring engaged with mating threads on the clamping jaws, (ii) a slip ring adapted to slide over the clamping jaws and to be held in place by friction or adhesive, or (iii) a snap ring adapted to engage a flange, tang, ratchet, or groove on the clamping jaws. Alternatively, the longitudinally-extending segments can be arranged to engage one another (by a linear ratchet, grooves, or other mechanism) to retain the clamping jaws 1220 engaged with the anatomical structure 1000.

The laterally-extending clamping jaws 1220 can be held in an elongated configuration by the delivery device 1210 as they are advanced and assume a laterally-extending shape upon emerging from the leading end of the delivery device 1210 (FIG. 12C). It may be desirable to fabricate the laterally-extending clamping jaws 1220 from a shape-memory alloys such as those disclosed hereinabove.

FIG. 13A illustrates schematically another exemplary apparatus and method for occluding an anatomical structure. The method comprises: providing near-real-time imaging of a target region of a body of a patient, the target region including an occlusion site on the anatomical structure 1000; introducing percutaneously into the body of the patient an elongated, tubular delivery device 1310; under guidance of the imaging, advancing the delivery device 1310 to an occlusion site outside the lumen 1001 of the anatomical structure 1000; and under guidance of the imaging, advancing a wire segment 1320 through the leading end of the delivery device 1310 so that the emerging end of the wire segment 1310 wraps around the anatomical structure 1000 as it is advanced. The wire segment 1320 is held in an elongated configuration by the delivery device as it is advanced and assumes a looped shape upon emerging from the leading end of the delivery device 1320. The curvature of the looped shape is sufficiently small so that the wrapped wire segment 1320 engages the exterior of the anatomical structure 1000 thereby occluding it.

As with previously described embodiments, if the occlusion is temporary, then the wrapped wire segment 1320 can be withdrawn into the leading end of the delivery device 1310, thereby disengaging it from the anatomical structure 1000. The wire segment 1320 and the delivery device 1310 can then be withdrawn from the body of the patient. If the occlusion is intended to be substantially permanent, then wrapped wire segment 1320 can be detached from the delivery device 1310 and left engaging the anatomical structure 1000 and occluding it when the delivery device 1210 is withdrawn from the occlusion site and the patient's body. The wire segment 1320 can be secured to the delivery device in any of the ways disclosed above for enabling it to be detached from the delivery device 1310. The wire segment 1320 or the delivery device 1310 can be used to cauterize (e.g., by electro-cautery) the anatomical structure at the occlusion site during or after deploying the wire segment. Alternatively, a separate cauterizer can be introduced to the occlusion site, either through delivery device 1310 or through an independent delivery device.

The wire segment 1320 can be held in an elongated configuration by the delivery device 1310 as they are advanced and assume a wrapped or looped shape upon emerging from the leading end of the delivery device 1310 (FIGS. 12A and 12B). It may be desirable to fabricate the wire segment 1320 from a shape-memory alloys such as those disclosed hereinabove.

The wrapped portion of the wire segment 1320 can be adapted so that it's curvature decreases upon being separated from the rest of the wire segment. For example, the wire segment can comprise a solid inner wire surrounded by an outer wire coil, with the inner wire and outer coil secured to one another at their respective ends thus limiting the curvature achieved as the wire segment emerges from the delivery device 1310 and wraps around the anatomical structure 1000. Limiting the curvature may reduce the likelihood of undesirable piercing of the anatomical structure by the end of the wire segment 1320. Once the wire segment 1320 is wrapped around the anatomical structure, the wrapped portion of the wire segment can be cut or otherwise separated from the reminder of the wire segment. This releases one end of the inner wire and outer coil from one another and allowed the wrapped wire segment to curl tighter around the anatomical structure.

In a variant of this embodiment (FIG. 13B), the ends of the wire segment are secured to one another. For example, a ring 1330 can be placed over the ends of the wrapped wire segment 1320 so as to retain it engaged with the anatomical structure 1000. Such a ring can comprise (i) a threaded ring engaged with mating threads on the wire segment, (ii) a slip ring adapted to slide over the ends of the wire segment and to be held in place by friction or adhesive, or (iii) a snap ring adapted to engage a flange, tang, ratchet, or groove on the wire segment.

FIG. 14A illustrates schematically another exemplary apparatus and method for occluding an anatomical structure. The method comprises: providing near-real-time imaging of a target region of a body of a patient, the target region including an occlusion site on the anatomical structure 1000; introducing percutaneously into the body of the patient an elongated, tubular delivery device 1410; under guidance of the imaging, advancing the delivery device 1410 to an occlusion site outside the lumen of the anatomical structure 1000 and through a first wall 1002 of the anatomical structure; under guidance of the imaging, advancing an occlusion member 1420 through the leading end of the delivery device 1410 into the lumen 1001 of the anatomical structure 1000; and expanding that portion of the occlusion member within the lumen to form an embolization structure 1420 within the lumen 1001, thereby causing occlusion of the anatomical structure 1000. The reference numeral 1420 refers to the occlusion member prior to expansion and to the resulting embolization structure after expansion.

As with previously described embodiments, if the occlusion is temporary, then the embolization structure 1430 can be contracted and the occlusion member 1420 and the delivery device 1410 can be withdrawn from the body of the patient. If the occlusion is intended to be substantially permanent, then embolization structure 1420 can be detached from the delivery device 1410 and left in the lumen 1001 occluding the anatomical structure 1000 when the delivery device 1410 is withdrawn from the occlusion site and the patient's body. The embolization structure 1420 can be secured to the delivery device in any of the ways disclosed above for enabling it to be detached from the delivery device 1410. The occlusion member 1420 can include an anchor portion 1440 extending through the wall of the anatomical structure 1000 so as to retain the occlusion member at the occlusion site (FIG. 14B).

The occlusion member or embolization structure 1420 or the delivery device 1410 can be used to cauterize (e.g., by electro-cautery) the anatomical structure 1000 at the occlusion site during or after deploying the embolization structure 1420. Alternatively, a separate cauterizer can be introduced to the occlusion site, either through delivery device 1410 or through an independent delivery device.

To enhance the occlusion of the embolization structure 1420 (e.g., by promoting clotting in a blood vessel), it can include one or more filaments within the lumen. The embolization structure 1420 can be arranged as a coil, a spiral, a knot, a cylinder or tube, or a random tangle. The embolization structure 1420 can be biodegradable or bioabsorbable. The embolization structure 1420 can be at least partly coated or treated with a physical, chemical, pharmaceutical, or other agent.

The occlusion member 1420 can be held in a compressed configuration while advanced from the leading end of delivery device 1410 and through the wall of the anatomical structure 1000, and can assume an expanded configuration once in the lumen (becoming embolization structure 1420). It may be desirable to fabricate the embolization structure 1420 from a shape-memory alloys such as those disclosed hereinabove.

Figure 15A:
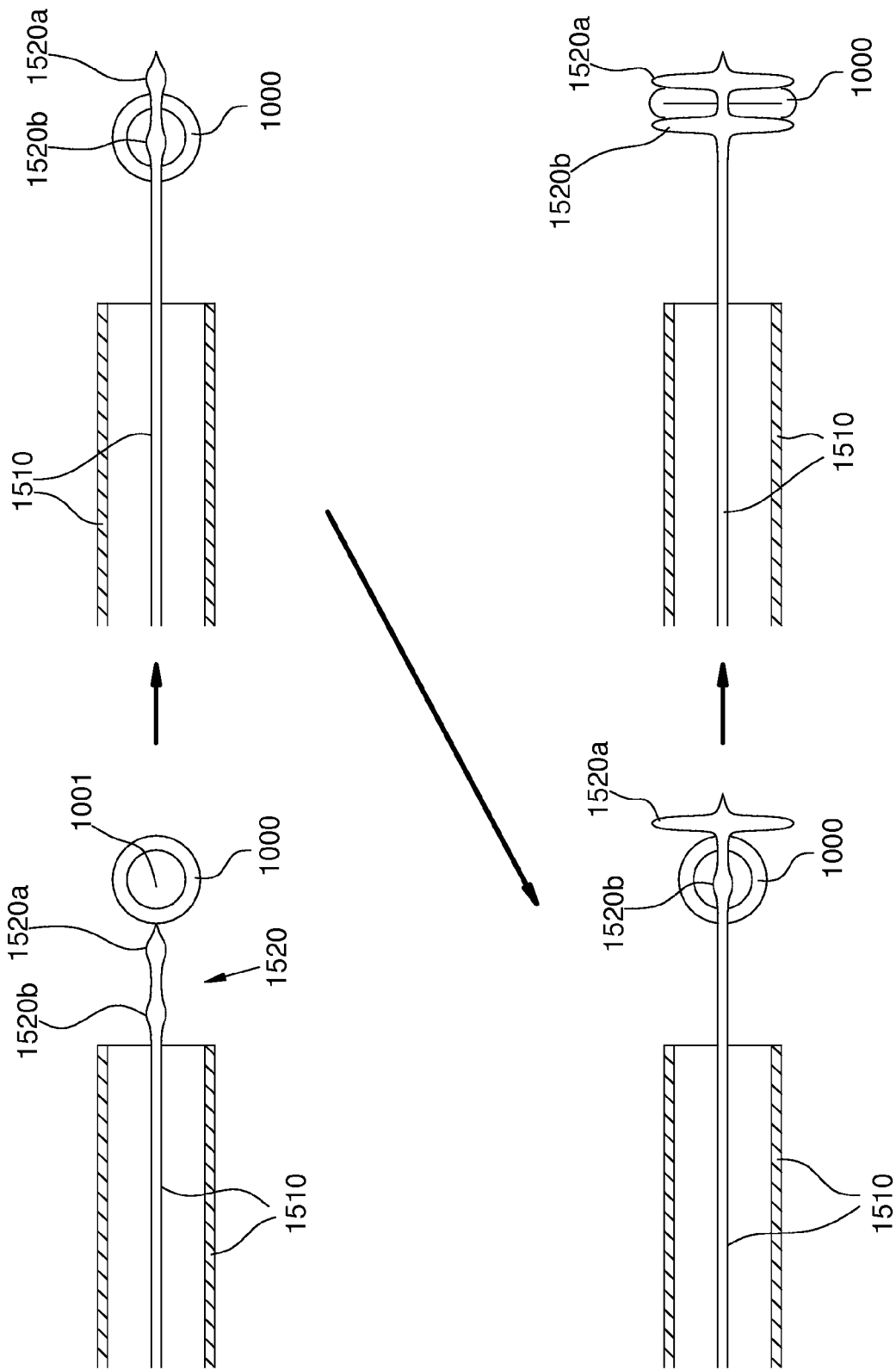

FIG. 15A illustrates schematically another apparatus and method for occluding an anatomical structure (somewhat analogous to FIGS. 9A-9E). The method comprises: providing near-real-time imaging of a target region of a body of a patient, the target region including an occlusion site on the anatomical structure 1000; introducing percutaneously into the body of the patient an elongated, tubular delivery device 1510; under guidance of the imaging, advancing the delivery device 1510 to an occlusion site on the anatomical structure 1000; under guidance of the imaging, advancing a deformable occlusion member 1520 through the leading end of the delivery device 1510, the deformable occlusion member comprising first and second transversely expandable segments 1520a and 1520b; and expanding the expandable segments 1520a and 1520b with the anatomical structure 1000 longitudinally between them, thereby engaging the exterior of the anatomical structure 1000 and occluding it.

As with previously described embodiments, if the occlusion is temporary, then the deformable occlusion member 1520 can be disengaged from the anatomical structure 1000 and the deformable occlusion member 1520 and the delivery device 1510 can be withdrawn from the body of the patient. If the occlusion is intended to be substantially permanent, then the deformable occlusion member 1520 can be detached from the delivery device 1510 and left engaging the anatomical structure 1000 and occluding it when the delivery device 1510 is withdrawn from the occlusion site and the patient's body. The deformable occlusion member 1520 can be secured to the delivery device 1520 in any of the ways disclosed above for enabling it to be detached from the delivery device 1510. The deformable occlusion member 1520 or the delivery device 1510 can be used to cauterize (e.g., by electro-cautery) the anatomical structure at the occlusion site during or after expanding the segments 1520a and 1520b. Alternatively, a separate cauterizer can be introduced to the occlusion site, either through delivery device 1510 or through an independent delivery device. It may be desirable to fabricate the expandable segments 1520a and 1520b from a shape-memory alloys such as those disclosed hereinabove.

As illustrated in FIG. 15A, the deformable occlusion member 1520 is typically advanced through a first wall of the anatomical structure 1000, across the lumen 1001, and through a second wall of the anatomical structure 1000. The first expandable segment 1520a is transversely expanded after it has passed through the second wall of the anatomical structure 1000. The deformable occlusion member 1520 is retracted to urge the expanded first segment 1520a against the outside of the second wall and to position the second expandable segment 1520b outside the first wall. The second segment 1520b is then transversely expanded outside the first wall, so that the expanded segments engage opposite side of the anatomical structure 1000 and compress it. Instead of advancing the deformable occlusion member 1520 through the anatomical structure 1000, it can instead be positioned next to the anatomical structure 1000 so that the expanded segments 1520a and 1520b still engage opposite side of the anatomical structure 1000 and compress it between them.

End views shown in FIGS. 15B and 15C illustrate alternative configurations of the expanded segments 1520a and 1520b (only 1520a visible in the views shown). In FIG. 15B the expandable segments are shown expanding only in two radially opposed directions, while in FIG. 15C the expandable segments are shown expanding in multiple radial directions.

Figure 16A:
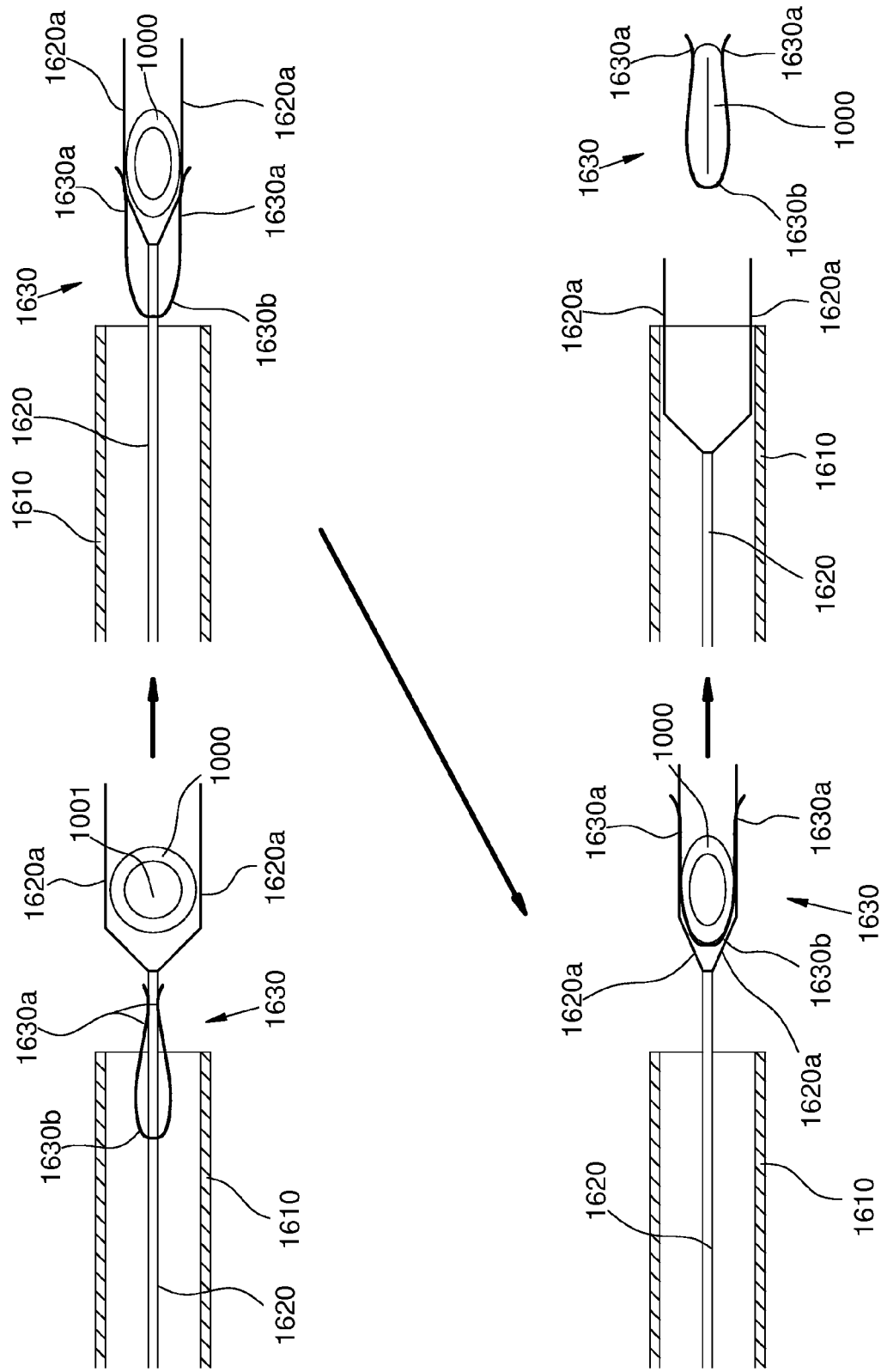
FIGS. 16A-16F illustrate schematically another exemplary embodiment of an extraluminal occlusion instrument.
Figure 16B:
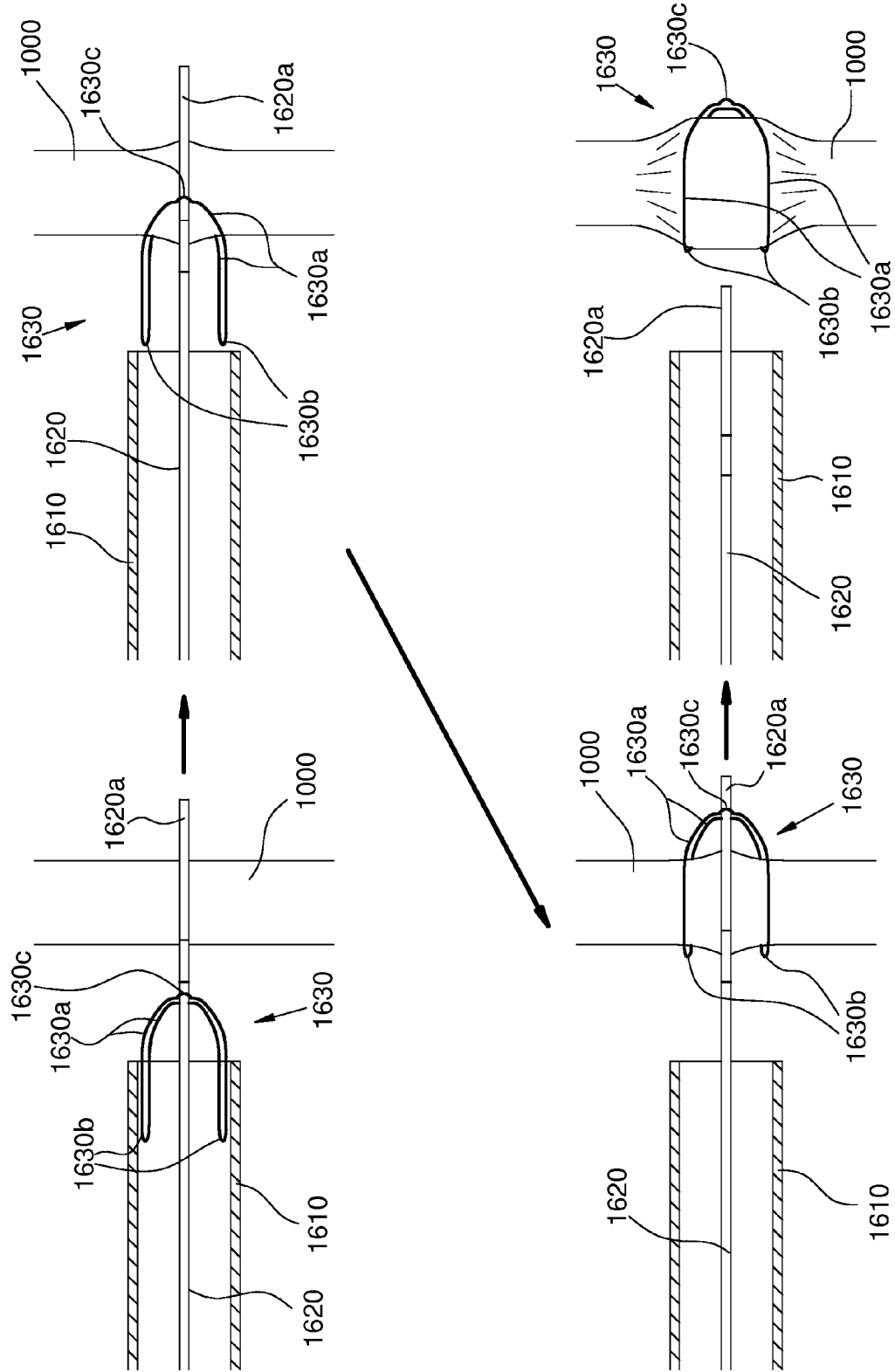

FIGS. 16A and 16B (side and top views, respectively) illustrate schematically another apparatus and method for occluding an anatomical structure. The method comprises: providing near-real-time imaging of a target region of a body of a patient, the target region including an occlusion site on the anatomical structure 1000; introducing percutaneously into the body of the patient an elongated, tubular delivery device 1610; under guidance of the imaging, advancing the delivery device 1610 to an occlusion site outside the lumen of the anatomical structure 1000; under guidance of the imaging, advancing a clamp guide 1620 having opposing deformable guide jaws 1620a at its leading end through the leading end of the delivery device 1610, the guide jaws 1620a being in an open position upon being advanced from the delivery device 1610 so that the anatomical structure 1000 lies between the guide jaws 1620a; sliding a deformable clamp 1630 along the clamp guide 1620, the deformable clamp 1630 comprising a pair of opposed clamp jaws 1630a connected by a resilient member 1630b so that the clamp jaws 1630a are biased toward or past one another in the clamp's non-deformed state, the clamp jaws 1630a being biased toward one another against the clamp guide 1620 as the clamp 1630 slides along the clamp guide 1620; sliding the deformable clamp 1620 over the guide jaws 1610a, thereby forcing the clamp jaws 1630a open sufficiently to receive the anatomical structure 1000 therebetween and positioning the clamp 1630 with the anatomical structure therebetween; and withdrawing the clamp guide 1610, leaving the clamp 1630 engaging the exterior of the anatomical structure 1000 and occluding it.

Figure 16E:
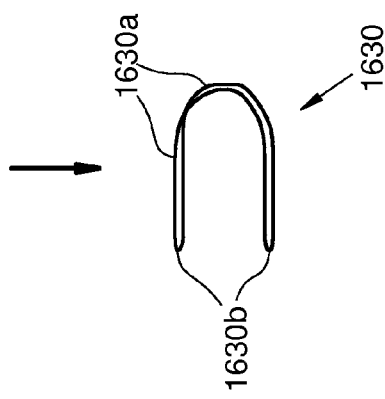
Figure 16F:
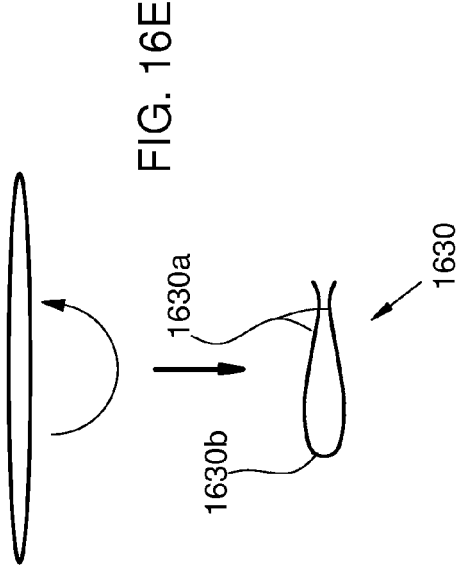
Figure 16C:
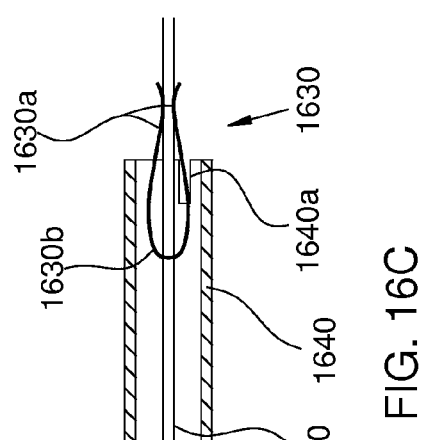
Figure 16D:
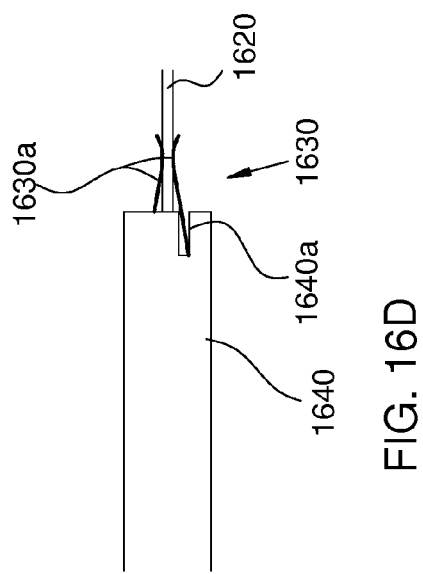

As shown in FIGS. 16C and 16D (cross-section and side views, respectively), a tubular pushing member 1640 can be arranged to slide along the clamp guide 1620 with the clamp guide 1620 received therethrough to urge the deformable clamp 1630 along the clamp guide 1620 and over the guide jaws 1620a. The pushing member 1640 can also be employed to retain the deformable clamp 1630 on the anatomical structure 1000 as the clamp guide 1620 is withdrawn. The tubular pushing member 1640 can have a pair of slots 1640a at its leading end arranged to receive the deformable clamp 1630 to limit roll of the deformable clamp 1630 as its slides along the clamp guide 1620. The clamp guide 1620 or the tubular pushing member 1640 can be indexed or otherwise arranged to limit relative roll thereof. The deformable clamp 1630 can be provided with a notch, groove, or detent 1630c on at least one of its clamp jaws 1630a that is arranged to engage the clamp guide 1620 to limit yaw of the deformable clamp 1630 as it slides along the clamp guide 1620.

As shown in FIGS. 16E and 16F (side and top views, respectively), the deformable clamp 1630 can comprise an elongated wire loop that is bent about its minor axis into a "U" shape so that the ends of the loop form the opposed clamp jaws. It may be desirable to fabricate the deformable clamp 1630 from a shape-memory alloys such as those disclosed hereinabove.

As with previously described embodiments, the clamp 1640, the clamp guide 1620, or the delivery device 1610 can be used to cauterize (e.g., by electro-cautery) the anatomical structure at the occlusion site during or after deploying the wire segment. Alternatively, a separate cauterizer can be introduced to the occlusion site, either through delivery device 1610 or through an independent delivery device.

It is intended that equivalents of the disclosed exemplary embodiments and methods shall fall within the scope of the present disclosure or appended claims. It is intended that the disclosed exemplary embodiments and methods, and equivalents thereof, may be modified while remaining within the scope of the present disclosure or appended claims.

For purposes of the present disclosure and appended claims, the conjunction "or" is to be construed inclusively (e.g., "a dog or a cat" would be interpreted as "a dog, or a cat, or both"; e.g., "a dog, a cat, or a mouse" would be interpreted as "a dog, or a cat, or a mouse, or any two, or all three"), unless: (i) it is explicitly stated otherwise, e.g., by use of "either . . . or", "only one of . . . ", or similar language; or (ii) two or more of the listed alternatives are mutually exclusive within the particular context, in which case "or" would encompass only those combinations involving non-mutually-exclusive alternatives.

For purposes of the present disclosure or appended claims, the words "include", "including", and so on shall be construed as being open-ended, e.g., "including" shall be construed as "including but not limited to".

What is claimed is:

1. A method for occluding an anatomical structure having a lumen, the method comprising:
providing near-real-time imaging of a target region of a body of a patient, the target region including an occlusion site on the anatomical structure;
introducing percutaneously into the body of the patient an elongated, tubular delivery device;
under guidance of the imaging and without direct or endoscopic visualization, advancing the delivery device through an extraluminal space within the patient's body to an occlusion site outside the lumen of the anatomical structure;
under guidance of the imaging and without direct or endoscopic visualization, advancing a deformable occlusion member through the leading end of the delivery device, the deformable occlusion member comprising first and second transversely expandable segments; and
expanding the expandable segments with the anatomical structure longitudinally between them, thereby engaging the exterior of the anatomical structure and occluding the anatomical structure wherein the act of advancing the deformable occlusion member includes advancing the deformable occlusion member through a first wall of the anatomical structure, across the lumen, and through a second wall of the anatomical structure; and the act of expanding the expandable segments includes transversely expanding the first expandable segment after it has passed through the second wall of the anatomical structure, retracting the deformable occlusion member to urge the expanded first expandable segment against the outside of the second wall and to position the second expandable segment outside the first wall, and expanding the second expandable segment outside the first wall.

2. The method of claim 1 further comprising cauterizing the anatomical structure at the occlusion site during or after expanding the expandable segments of the deformable occlusion member.

3. The method of claim 1 wherein the delivery device or the deformable occlusion member comprises multiple materials having differing imaging densities.

4. The method of claim 1 wherein the deformable occlusion member comprises a shape-memory alloy.

* * * * *